(12) United States Patent
Scheib et al.

(10) Patent No.: US 12,714,455 B2
(45) Date of Patent: Aug. 25, 2026

(54) ULTRASONIC SURGICAL INSTRUMENT WITH A MID-SHAFT CLOSURE SYSTEM AND RELATED METHODS

(71) Applicant: Cilag GmbH International, Zug (CH)

(72) Inventors: Charles J. Scheib, Loveland, OH (US); Andrew T. Beckman, Cincinnati, OH (US); Travis M. Schuh, Los Altos, CA (US); Benjamin D. Dickerson, San Francisco, CA (US)

(73) Assignee: CILAG GMBH INTERNATIONAL, Zug (CH)

( * ) Notice: Subject to any disclaimer, the term of this patent is extended or adjusted under 35 U.S.C. 154(b) by 162 days.

(21) Appl. No.: 18/589,601

(22) Filed: Feb. 28, 2024

(65) Prior Publication Data

US 2024/0197356 A1 Jun. 20, 2024

Related U.S. Application Data

(63) Continuation of application No. 17/077,110, filed on Oct. 22, 2020, now Pat. No. 11,944,341.

(51) Int. Cl.
*A61B 17/32* (2006.01)
*A61B 17/00* (2006.01)

(52) U.S. Cl.
CPC ................. *A61B 17/320092* (2013.01); *A61B 2017/00402* (2013.01); *A61B 2017/320075* (2017.08); *A61B 2017/320094* (2017.08)

(58) Field of Classification Search
CPC ............ A61B 17/2812; A61B 17/2816; A61B 17/295; A61B 17/32; A61B 17/320068;
(Continued)

(56) References Cited

U.S. PATENT DOCUMENTS 6,783,524 B2 8/2004 Anderson et al.
7,354,440 B2 4/2008 Truckai et al.
(Continued)

OTHER PUBLICATIONS

International Search Report and Written Opinion dated Jan. 14, 2022, for International Application No. PCT/IB2021/059598, 18 pages.

(Continued)

*Primary Examiner* — Robert A Lynch
(74) *Attorney, Agent, or Firm* — FBT Gibbons LLP

(57) ABSTRACT

An ultrasonic surgical instrument comprises a shaft assembly including a waveguide, and an end effector arranged at a distal end of the shaft assembly and including an ultrasonic blade and a clamp arm. The instrument also comprises a base translatably coupled to shaft assembly. The base includes a first mechanical input and a second mechanical input. The instrument further comprises a closure actuation mechanism operatively connected between the first mechanical input and the clamp arm and configured to actuate the clamp arm from an open position toward a closed position upon selective drive of the first mechanical input. The instrument also includes an insertion actuation mechanism operatively connected between the second mechanical input and the shaft assembly and configured to actuate the shaft assembly from a proximal position toward a distal position upon selective drive of the second mechanical input for insertion of the end effector.

19 Claims, 8 Drawing Sheets

(58) Field of Classification Search
CPC .. A61B 17/320092; A61B 2017/00309; A61B 2017/00314; A61B 2017/00323; A61B 2017/00402; A61B 2017/2927; A61B 2017/320016; A61B 2017/320069; A61B 2017/320071; A61B 2017/320074; A61B 2017/320075; A61B 2017/320082; A61B 2017/320093; A61B 2017/320094; A61B 34/30; A61B 34/37; A61B 34/71; A61B 2034/2051; A61B 2034/306
See application file for complete search history.

(56) References Cited

U.S. PATENT DOCUMENTS

| | | | |
|---|---|---|---|
| 7,381,209 | B2 | 6/2008 | Truckai et al. |
| 8,663,220 | B2 | 3/2014 | Wiener et al. |
| 8,986,302 | B2 | 3/2015 | Aldridge et al. |
| 9,949,785 | B2 | 4/2018 | Price et al. |
| 10,470,830 | B2 | 11/2019 | Hill et al. |
| 11,457,945 | B2 | 10/2022 | Hunter et al. |
| 11,471,181 | B2 | 10/2022 | Hunter et al. |
| 11,612,409 | B2 | 3/2023 | Black et al. |
| 11,690,642 | B2 | 7/2023 | Black et al. |
| 11,712,261 | B2 | 8/2023 | Hunter et al. |
| 11,806,037 | B2 | 11/2023 | Black et al. |
| 11,944,341 | B2 * | 4/2024 | Scheib ........... A61B 17/320092 |
| 2006/0079874 | A1 | 4/2006 | Faller et al. |
| 2007/0191713 | A1 | 8/2007 | Eichmann et al. |
| 2008/0200940 | A1 | 8/2008 | Eichmann et al. |
| 2017/0181765 | A1 | 6/2017 | Riestenberg et al. |
| 2019/0175287 | A1 | 6/2019 | Hill et al. |
| 2020/0022767 | A1 | 1/2020 | Hill et al. |
| 2021/0015572 | A1 | 1/2021 | Gomez et al. |
| 2021/0022815 | A1 | 1/2021 | Abbott |
| 2022/0125460 | A1 | 4/2022 | Black et al. |
| 2022/0125463 | A1 | 4/2022 | Black et al. |
| 2022/0125464 | A1 | 4/2022 | Black et al. |
| 2022/0125465 | A1 | 4/2022 | Beckman et al. |
| 2022/0125466 | A1 | 4/2022 | Beckman et al. |
| 2022/0125467 | A1 | 4/2022 | Black et al. |
| 2022/0125468 | A1 | 4/2022 | Scheib et al. |
| 2022/0125469 | A1 | 4/2022 | Black et al. |
| 2022/0125470 | A1 | 4/2022 | Black et al. |
| 2022/0125471 | A1 | 4/2022 | Black et al. |
| 2022/0125472 | A1 | 4/2022 | Beckman et al. |
| 2022/0125473 | A1 | 4/2022 | Black et al. |

OTHER PUBLICATIONS

U.S. Appl. No. 62/930,638 entitle "Articulation Joint with Helical Lumen," filed Nov. 5, 2019.

* cited by examiner

ULTRASONIC SURGICAL INSTRUMENT WITH A MID-SHAFT CLOSURE SYSTEM AND RELATED METHODS

CROSS-REFERENCE TO RELATED APPLICATION

This application claims priority to U.S. Non-provisional patent application Ser. No. 17/077,110, entitled "Ultrasonic Surgical Instrument with a Mid-shaft Closure System and Related Methods," filed Oct. 22, 2020, published as U.S. Pat. Pub. No. 2022/0125468 on Apr. 28, 2022, issued as U.S. Pat. No. Apr. 2, 2024, the disclosure of which is hereby incorporated by reference herein.

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

In one example, the end effector of the surgical instrument includes a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; and U.S. Pub. No. 2008/0200940, entitled "Ultrasonic Device for Cutting and Coagulating," published Aug. 21, 2008, now abandoned, the disclosure of which is incorporated by reference herein.

Examples of robotic systems, at least some of which have ultrasonic features and/or associated articulatable portions, include U.S. patent application Ser. No. 16/556,661, entitled "Ultrasonic Surgical Instrument with a Multi-Planar Articulating Shaft Assembly," filed on Aug. 30, 2019, issued as U.S. Pat. No. 11,690,642 on Jul. 4, 2023; U.S. patent application Ser. No. 16/556,667, entitled "Ultrasonic Transducer Alignment of an Articulating Ultrasonic Surgical Instrument," filed on Aug. 30, 2019, issued as U.S. Pat. No. 11,612,409 on Mar. 28, 2023; U.S. patent application Ser. No. 16/556,625, entitled "Ultrasonic Surgical Instrument with Axisymmetric Clamping," filed on Aug. 30, 2019, issued as U.S. Pat. No. 11,471,181 on Oct. 18, 2022; U.S. patent application Ser. No. 16/556,635, entitled "Ultrasonic Blade and Clamp Arm Alignment Features," filed on Aug. 30, 2019, issued as U.S. Pat. No. 11,457,945 on Oct. 4, 2022; U.S. patent application Ser. No. 16/556,727, entitled "Rotatable Linear Actuation Mechanism," filed on Aug. 30, 2019, issued as U.S. Pat. No. 11,712,261 on Aug. 1, 2023; and/or U.S. Pat. App. No. 62/930,638, entitled "Articulation Joint with Helical Lumen," filed on Nov. 5, 2019. The disclosure of each of these applications is incorporated by reference herein.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
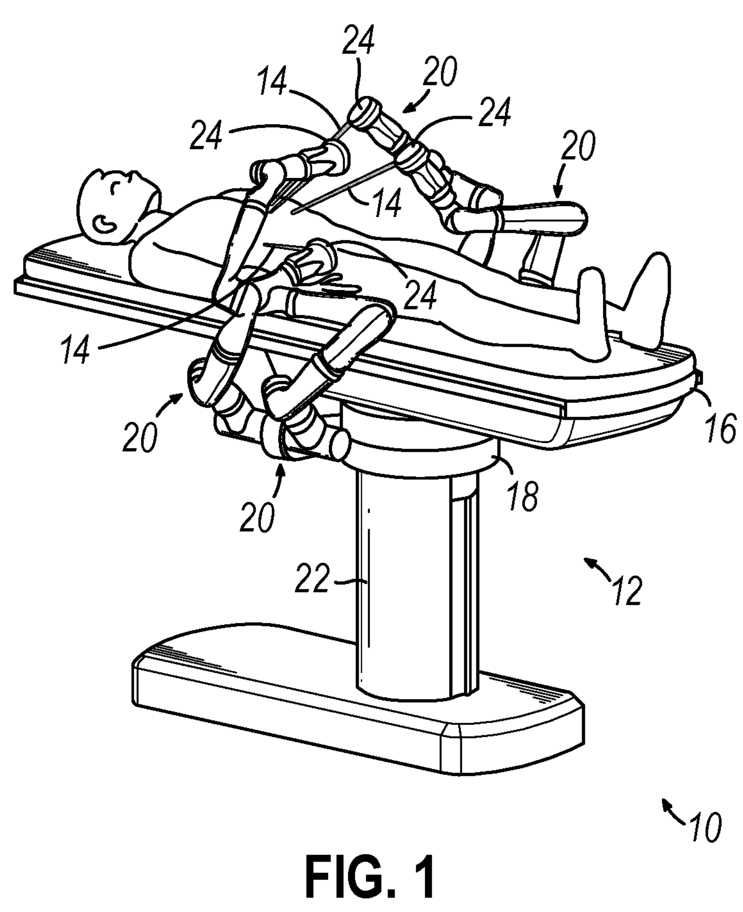
FIG. 1 depicts a perspective view of a first example of a table-based robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," and "transverse" also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. EXEMPLARY ROBOTICALLY-ENABLED MEDICAL SYSTEM

FIG. 1 shows an exemplary robotically-enabled medical system, including a first example of a table-based robotic system (10). Table-based robotic system (10) of the present example includes a table system (12) operatively connected to an instrument for a diagnostic and/or therapeutic procedure in the course of treating a patient. Such procedures may include, but are not limited, to bronchoscopy, ureteroscopy, a vascular procedure, and a laparoscopic procedure. To this end, the instrument illustrated in the present example is an ultrasonic surgical instrument (14) configured for a laparoscopic procedure, although it will be appreciated that any instrument for treating a patient may be similarly used. At least part of table-based robotic system (10) may be constructed and operable in accordance with at least some of the teachings of any of the various patents, patent application publications, and patent applications that are cited herein. As described therein and as will be described in greater detail below, ultrasonic surgical instrument (14) is operable to cut tissue and seal or weld tissue (e.g., a blood vessel, etc.) substantially simultaneously. While one or more examples incorporates various ultrasonic features, such as ultrasonic surgical instrument (14), the invention is not intended to be unnecessarily limited to the ultrasonic features described herein.

A. First Exemplary Table-Based Robotic System

With respect to FIG. 1, table-based robotic system (10) includes table system (12) having a platform, such as a table (16), with a plurality of carriages (18) which may also be referred to herein as "arm supports," respectively supporting the deployment of a plurality of robotic arms (20). Table-based robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate ultrasonic surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as ultrasonic surgical instrument (14) into different access points on the patient. In alternative examples, such as those discussed below in greater detail, table-based robotic system (10) may include a patient table or bed with adjustable arm supports including a bar (26) (see FIG. 2) extending alongside. One or more robotic arms (20) (e.g., via a shoulder with an elbow joint) may be attached to carriages (18), which are vertically adjustable so as to be stowed compactly beneath the patient table or bed, and subsequently raised during use.

Table-based robotic system (10) may also include a tower (not shown) that divides the functionality of table-based robotic system (10) between table (16) and the tower to reduce the form factor and bulk of table (16). To this end, the tower may provide a variety of support functionalities to table (16), such as processing, computing, and control capabilities, power, fluidics, and/or optical and sensor processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In one example, the tower may include gas tanks to be used for insufflation.

B. Second Exemplary Table-Based Robotic System

Figure 2:
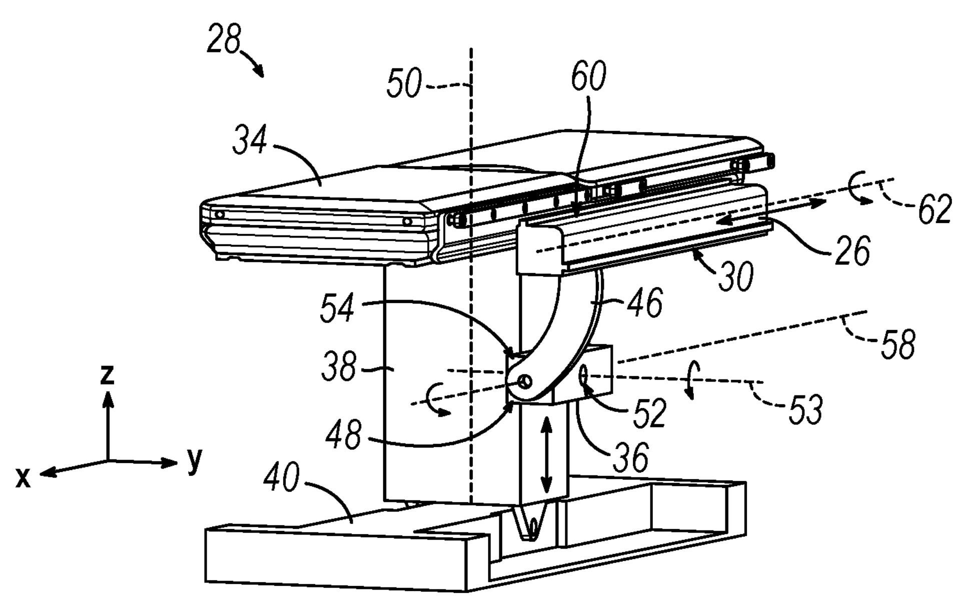
FIG. 2 depicts a perspective view of a second example of a table-based robotic system.
Figure 3:
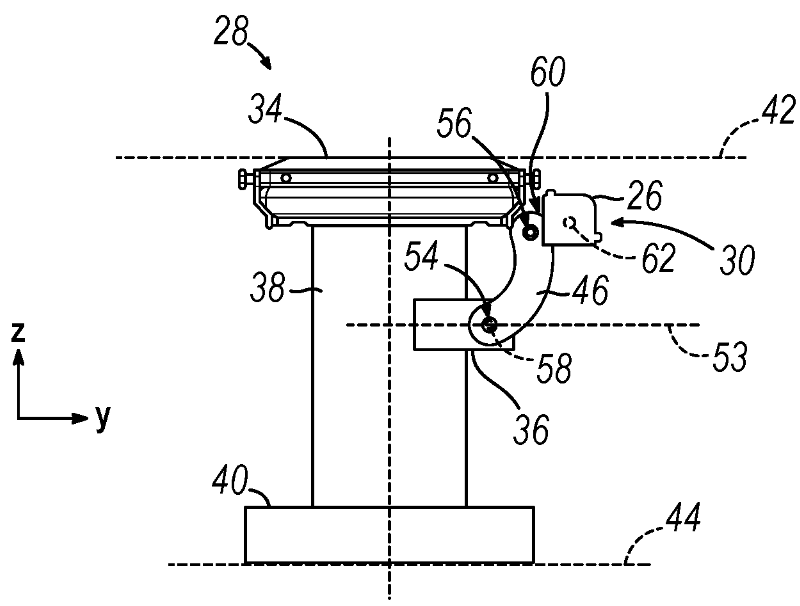
FIG. 3 depicts an end elevational view of the table-based robotic system of FIG. 2.
Figure 4:
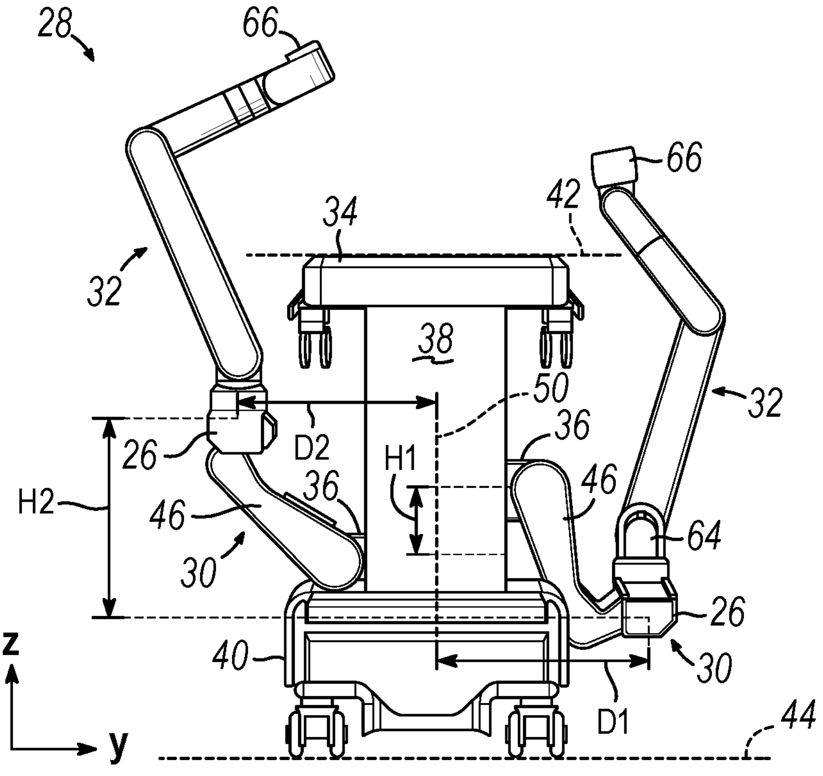
FIG. 4 depicts the end elevational view of the table-based robotic system of FIG. 3 including a pair of exemplary robotic arms.

As discussed briefly above, a second exemplary table-based robotic system (28) includes one or more adjustable arm supports (30) including bars (26) configured to support one or more robotic arms (32) relative to a table (34) as shown in FIGS. 2-4. In the present example, a single and a pair of adjustable arm supports (30) are shown, though additional arm supports (30) may be provided about table (34). Adjustable arm support (30) is configured to selectively move relative to table (34) so as to alter the position of adjustable arm support (30) and/or any robotic arms (32) mounted thereto relative to table (34) as desired. Such adjustable arm supports (30) provide high versatility to table-based robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36) configured to move up or down along or relative to a column (38) and a base (40) supporting table (34). A second degree of freedom allows adjustable arm support (30) to tilt about an axis extending in the y-direction. For example, adjustable arm support (30) includes a rotary joint, which allows adjustable arm support (30) to align the bed in a Trendelenburg position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) support table (34) relative to a support surface, which is shown along a support axis (42) above a floor axis (44) and in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

With respect to FIG. 4, table-based robotic system (28) is shown with two adjustable arm supports (30) mounted on opposite sides of table (34). A first robotic arm (32) is attached to one such bar (26) of first adjustable arm support (30). First robotic arm (32) includes a base (64) attached to bar (26). Similarly, second robotic arm (32) includes base (64) attached to other bar (26). Distal ends of first and second robotic arms (32) respectively include instrument drivers (66), which are configured to attach to one or more instruments such as those discussed below in greater detail.

In one example, one or more robotic arms (32) has seven or more degrees of freedom. In another example, one or more robotic arms (32) has eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (64) (1-degree of freedom including translation). In one example, the insertion degree of freedom is provided by robotic arm (32), while in another example, such as ultrasonic surgical instrument (14) (see FIG. 6A), the instrument includes an instrument-based insertion architecture.

Figure 5:
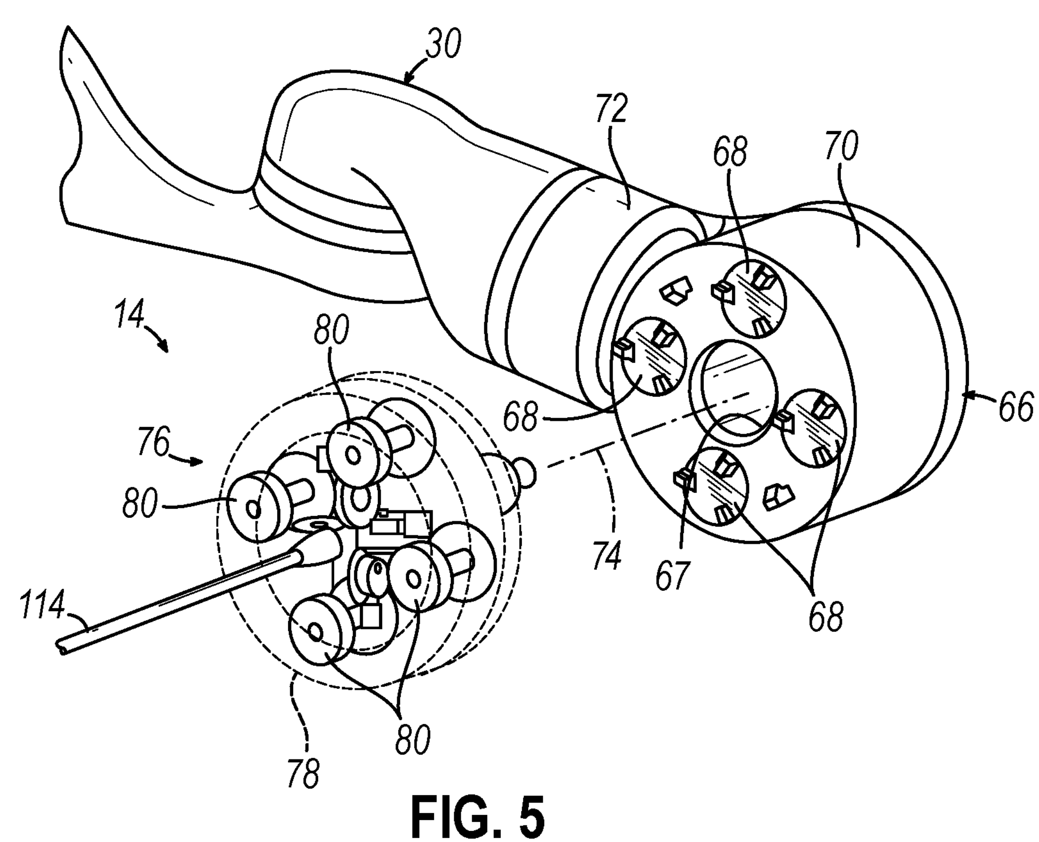
FIG. 5 depicts a partially exploded perspective view of the robotic arm of FIG. 4 having an instrument driver and a first exemplary surgical instrument.

FIG. 5 shows one example of instrument driver (66) in greater detail with ultrasonic surgical instrument (14) removed therefrom. Given the present instrument-based insertion architecture shown with reference to ultrasonic surgical instrument (14), instrument driver (66) further includes a clearance bore (67) extending entirely therethrough so as to movably receive a portion of ultrasonic surgical instrument (14) as discussed below in greater detail. Instrument driver (66) may also be referred to herein as an "instrument drive mechanism," an "instrument device manipulator," or an "advanced device manipulator" (ADM). Instruments may be designed to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of ultrasonic surgical instrument (14). Instrument driver (66) and ultrasonic surgical instrument (14) of the present example are aligned such that the axes of each drive output (68) are parallel to the axis of ultrasonic surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with ultrasonic surgical instrument (14) as a single unit around an instrument driver axis (74).

Any systems described herein, including table-based robotic system (28), may further include an input controller (not shown) for manipulating one or more instruments. In some embodiments, the input controller (not shown) may be coupled (e.g., communicatively, electronically, electrically, wirelessly and/or mechanically) with an instrument such that manipulation of the input controller (not shown) causes a corresponding manipulation of the instrument e.g., via master slave control. In one example, one or more load cells (not shown) may be positioned in the input controller such that portions of the input controller (not shown) are capable of operating under admittance control, thereby advantageously reducing the perceived inertia of the controller while in use.

In addition, any systems described herein, including table-based robotic system (28) may provide for non-radiation-based navigational and localization means to reduce exposure to radiation and reduce the amount of equipment within the operating room. As used herein, the term "localization" may refer to determining and/or monitoring the position of objects in a reference coordinate system. Technologies such as pre-operative mapping, computer vision, real-time electromagnetic sensor (EM) tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

C. First Exemplary Ultrasonic Surgical Instrument

Figure 6A:
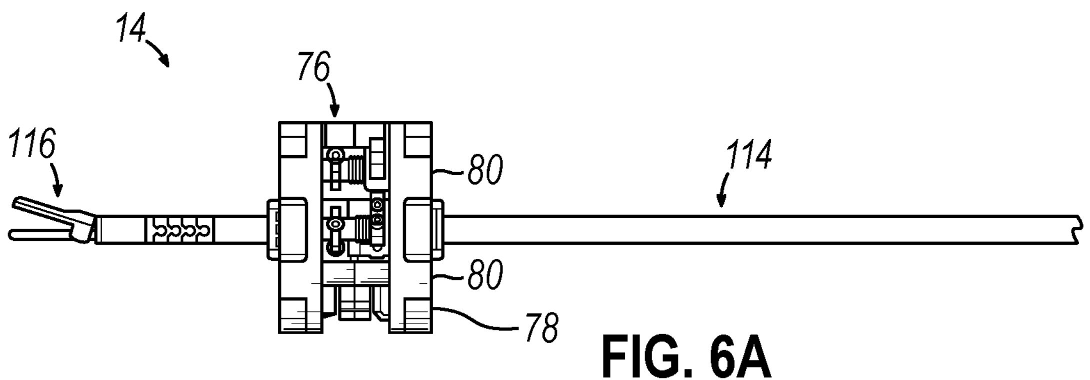
FIG. 6A depicts a side elevational view of the surgical instrument of FIG. 5 in a retracted position.
Figure 6B:
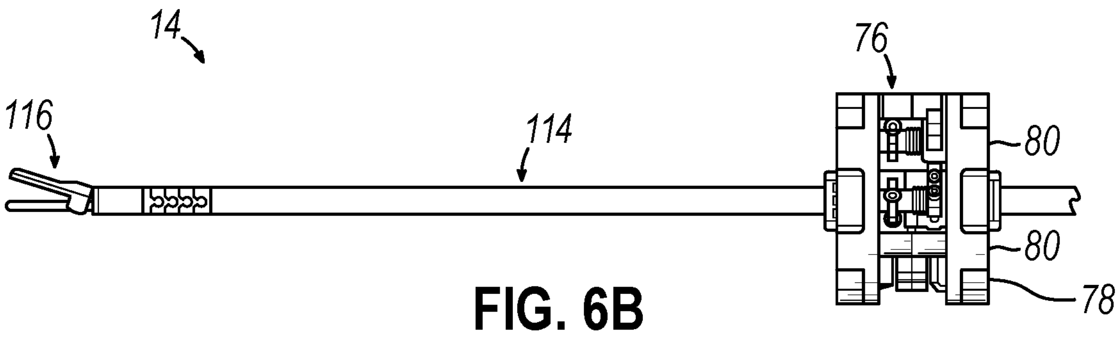
FIG. 6B depicts the side elevational view the surgical instrument similar to FIG. 6A, but in an extended position.

With respect to FIGS. 5-6B and in cooperation with instrument driver (66) discussed above, ultrasonic surgical instrument (14) includes an elongated shaft assembly (114) and an instrument base (76) with an attachment interface (78) having a plurality of drive inputs (80) configured to respectively couple with corresponding drive outputs (68). Shaft assembly (114) of ultrasonic surgical instrument (14) extends from a center of base (76) with an axis substantially parallel to the axes of the drive inputs (80) as discussed briefly above. With shaft assembly (114) positioned at the center of base (76), shaft assembly (114) is coaxial with instrument driver axis (74) when attached and movably received in clearance bore (67). Thus, rotation of rotational assembly (70) causes shaft assembly (114) of ultrasonic surgical instrument (14) to rotate about its own longitudinal axis while clearance bore (67) provides space for translation of shaft assembly (114) during use.

To this end, FIGS. 5-6B show ultrasonic surgical instrument (14) having the instrument-based insertion architecture as discussed briefly above. Ultrasonic surgical instrument (14) includes elongated shaft assembly (114), an end effector (116) connected to and extending distally from shaft assembly (114), and instrument base (76) coupled to shaft assembly (114). Notably, insertion of shaft assembly (114) is grounded at instrument base (76) such that end effector (116) is configured to selectively move longitudinally from a retracted position to an extended position, vice versa, and any desired longitudinal position therebetween. As used herein, the retracted position is shown in FIG. 6A and places end effector (116) relatively close and proximally toward instrument base (76), whereas the extended position is shown in FIG. 6B and places end effector (116) relatively far and distally away from instrument base (76). Insertion into and withdrawal of end effector (116) relative to the patient may thus be facilitated by ultrasonic surgical instrument (14), although it will be appreciated that such insertion into and withdrawal may also occur via adjustable arm supports (30) in one or more examples.

While the present example of instrument driver (66) shows drive outputs (68) arranged in rotational assembly (70) so as to face in a distal direction like distally projecting end effector (116) from shaft assembly (114), an alternative instrument driver (not shown) may include drive output (68) arranged on an alternative rotational assembly (70) to face in a proximal direction, opposite of the distally projecting end effector (116). In such an example, ultrasonic surgical instrument (14) may thus have drive inputs (80) facing distally to attach to instrument drivers (66) facing proximally in an opposite direction from that shown in FIG. 5. The invention is thus not intended to be unnecessarily limited to the particular arrangement of drive outputs (68) and drive inputs (80) shown in the present example and any such arrangement for operatively coupling between drive outputs and inputs (68, 80) may be similarly used.

While various features configured to facilitate movement between end effector (116) and drive inputs (80) are described herein, such features may additionally or alternatively include pulleys, cables, carriers, such as a kinetic articulating rotating tool (KART), and/or other structures configured to communicate movement along shaft assembly (114). Moreover, while instrument base (76) is configured to operatively connect to instrument driver (66) for driving various features of shaft assembly (114) and/or end effector (116) as discussed below in greater detail, it will be appreciated that alternative examples may operatively connect shaft assembly (114) and/or end effector (116) to an alternative handle assembly (not shown). Such handle assembly (not shown) may include a pistol grip (not shown) in one example, configured to be directly gripped and manipulated by the medical professional for driving various features of shaft assembly (114) and/or end effector (116). The invention is thus not intended to be unnecessarily limited to use with instrument driver (66).

i. First Exemplary End Effector and Acoustic Drivetrain

Figure 7A:
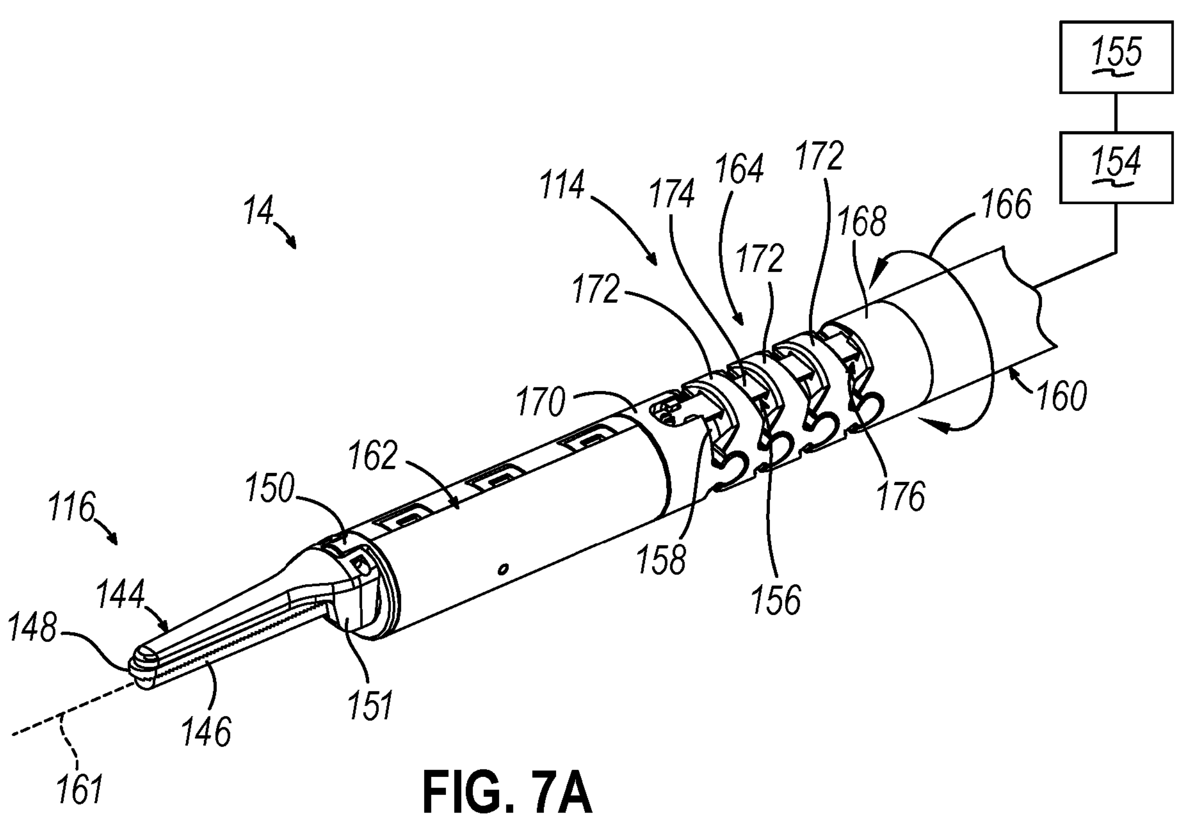
FIG. 7A depicts an enlarged perspective view of the surgical instrument of FIG. 6A with an end effector in a closed position and a shaft assembly in a straight configuration.
Figure 7B:
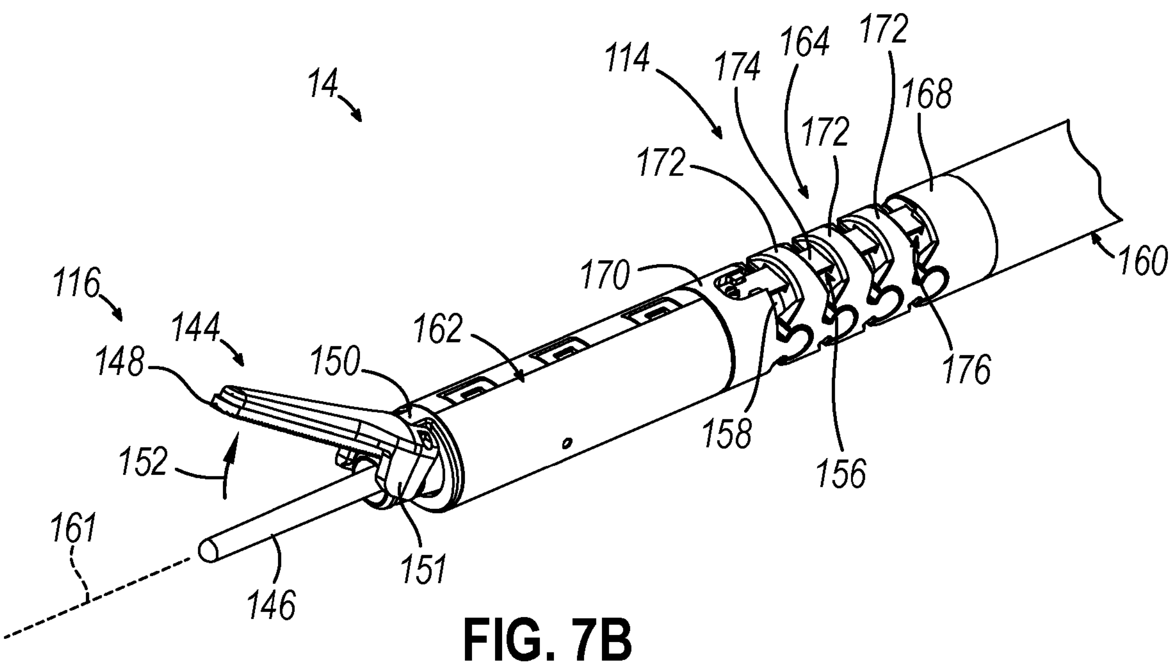
FIG. 7B depicts the enlarged perspective view of the surgical instrument similar to FIG. 7A, but showing the end effector in an open position.

As best seen in FIGS. 7A-7B, end effector (116) of the present example includes a clamp arm (144) and an ultrasonic blade (146). Clamp arm (144) has a clamp pad (148) secured to an underside of clamp arm (144), facing blade (146). Clamp arm (144) is pivotally secured to a distally projecting tongue (150) of shaft assembly (114). Clamp arm (144) is operable to selectively pivot toward and away from blade (146) to selectively clamp tissue between clamp arm (144) and blade (146). A pair of arms (151) extend transversely from clamp arm (144) and are pivotally secured to another portion of shaft assembly (114) configured to longitudinally slide to pivot clamp arm (144) as indicated by an arrow (152) between a closed position shown in FIG. 7A and an open position shown in FIG. 7B.

Blade (146) of the present example is operable to vibrate at ultrasonic frequencies in order to effectively cut through and seal tissue, particularly when the tissue is being compressed between clamp pad (148) and blade (146). Blade (146) is positioned at a distal end of an acoustic drivetrain. This acoustic drivetrain includes a transducer assembly (154) and an acoustic waveguide (156), which includes a flexible portion (158) discussed below in greater detail.

Transducer assembly (154) is further connected to a generator (155) of the acoustic drivetrain. More particularly, transducer assembly (154) is coupled with generator (155) such that transducer assembly (154) receives electrical power from generator (155). Piezoelectric elements (not shown) in transducer assembly (154) convert that electrical power into ultrasonic vibrations. By way of example only, generator (155) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

When transducer assembly (154) of the present example is activated, mechanical oscillations are transmitted through waveguide (156) to reach blade (146), thereby providing oscillation of blade (146) at a resonant ultrasonic frequency (e.g., 55.5 kHz). Thus, when tissue is secured between blade (146) and clamp pad (148), the ultrasonic oscillation of blade (146) may simultaneously sever the tissue and denature the proteins in adjacent tissue cells, thereby providing a coagulative effect with relatively little thermal spread.

ii. First Exemplary Shaft Assembly and Articulation Section

As shown in FIGS. 7A-7B, shaft assembly (114) includes a proximal shaft portion (160) extending along a longitudinal axis (161), a distal shaft portion (162) distally projecting relative to proximal shaft portion (160), and an articulation section (164) extending between proximal and distal shaft portions (160, 162). Shaft assembly (114) is configured to rotate about longitudinal axis (161) as indicated by an arrow (166). In one example, shaft assembly (114) rotates in the clockwise or counterclockwise directions completely around longitudinal axis (161) and may be selectively fixed in any rotational position about longitudinal axis (161) for positioning articulation section (164) and/or end effector (116) about longitudinal axis (161).

Articulation section (164) is configured to selectively position end effector (116) at various lateral deflection angles relative to longitudinal axis (161) defined by proximal shaft portion (160). Articulation section (164) may take a variety of forms. In the present example, articulation section (164) includes a proximal link (168), a distal link (170), and a plurality of intermediate links (172) connected in series between proximal and distal links (168, 170). Articulation section (164) further includes a pair of articulation bands (174) extending along a pair of respective channels (176) collectively defined through links (168, 170, 172). Links (168, 170, 172) are generally configured to pivot relative to each other upon actuation of articulation bands (174) to thereby bend articulation section (164) with flexible portion (158) of waveguide (156) therein to achieve an articulated state.

Figure 8A:
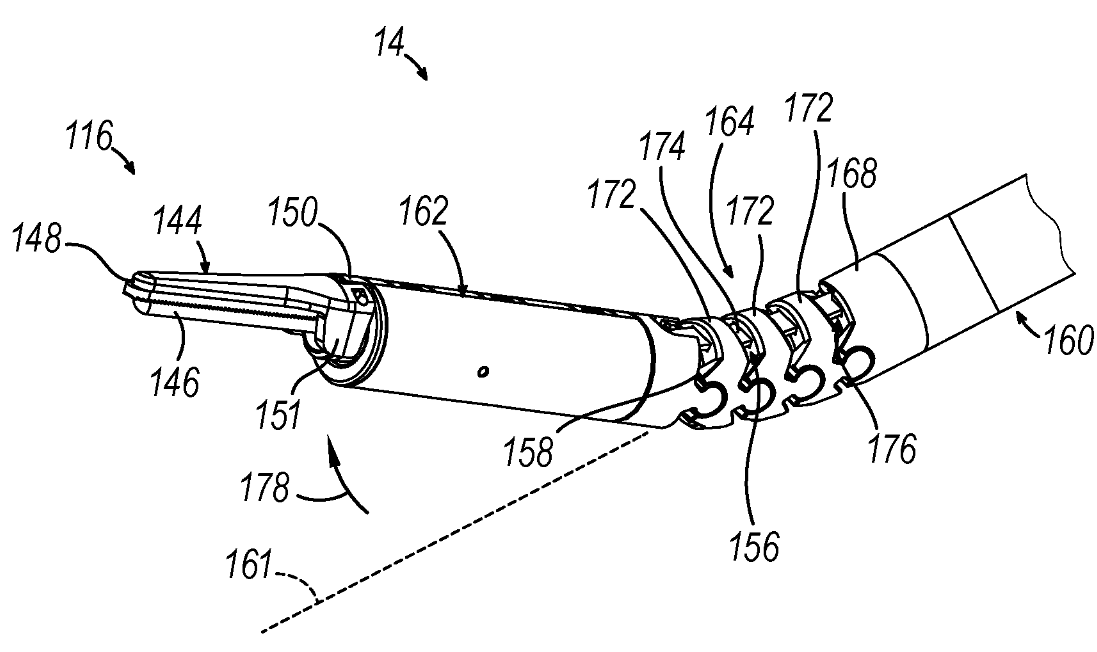
FIG. 8A depicts an enlarged perspective view of the surgical instrument of FIG. 6A with the end effector in a closed position and the shaft assembly in a first articulated configuration.
Figure 8B:
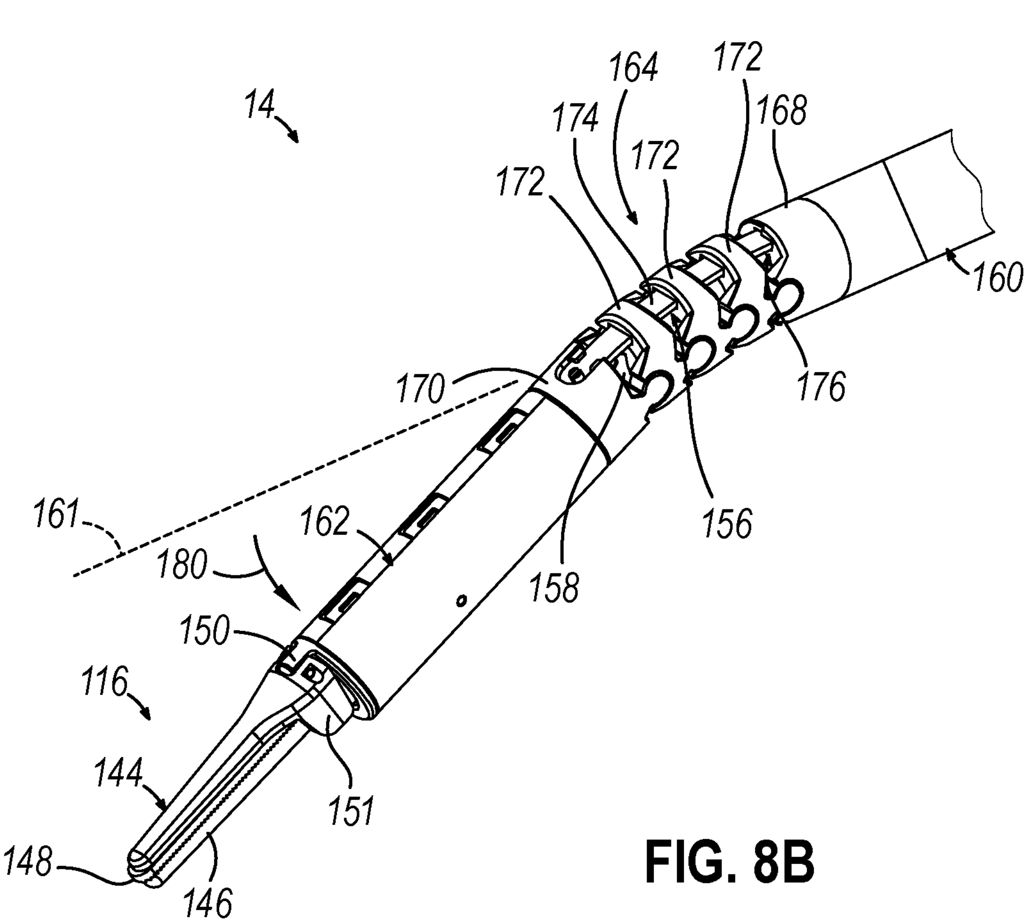
FIG. 8B depicts the enlarged perspective view of the surgical instrument similar to FIG. 8A, but with the shaft assembly in a second articulated configuration.

Links (168, 170, 172) shown in FIGS. 7B-8B pivotally interlock to secure distal shaft portion (162) relative to proximal shaft portion (160) while allowing for deflection of distal shaft portion (162) relative to longitudinal axis (161). Thus, as a pair of articulation bands (174) translate longitudinally in an opposing fashion, this will cause articulation section (164) to bend via links (168, 170, 172) thereby laterally deflecting end effector (116) away from the longitudinal axis (161) of proximal shaft portion (160) from a straight configuration as shown in FIG. 7B to a first articulated configuration as shown in FIG. 8A and indicated by an arrow (178) or a second articulated configuration as shown in FIG. 8B and indicated by an arrow (180). Furthermore, flexible acoustic waveguide (156) is configured to effectively communicate ultrasonic vibrations from waveguide (156) to blade (146) even when articulation section (164) is in an articulated configuration as shown in FIGS. 8A-8B.

II. EXEMPLARY ULTRASONIC SURGICAL INSTRUMENT WITH MID-SHAFT CLOSURE SYSTEM

In some instances, it may be desirable to provide an ultrasonic surgical instrument having an instrument-based insertion architecture that not only allows for insertion of the instrument, but also allows a clamp arm of an end effector of the instrument to actuate without interference. For example, it may be desirable to provide an ultrasonic surgical instrument having a closure actuation mechanism for actuating an end effector of the instrument and an insertion actuation mechanism for causing translation of a portion of the instrument (e.g., a shaft) along an axis of insertion. It may be further desirable to provide such an ultrasonic surgical instrument wherein the closure actuation mechanism is decoupled from the insertion actuation mechanism such that the actuation of the end effector is not affected by the insertion of the instrument, and vice versa. FIGS. 9A-9D show a second exemplary ultrasonic surgical instrument (210) having such capabilities. Ultrasonic surgical instrument (210) is similar to ultrasonic surgical instrument (14) described above except as otherwise described below such that like numbers indicate like features.

A. Overview of Second Exemplary Ultrasonic Surgical Instrument

As shown in FIGS. 9A-9D, ultrasonic surgical instrument (210) includes a proximal housing (212), an elongated shaft assembly (214) extending distally from proximal housing (212), an end effector (216) extending distally from shaft assembly (214), and an instrument base (218) translatably coupled to shaft assembly (214). In this regard, instrument base (218) includes a body (219) with an attachment interface (220) having a plurality of mechanical drive inputs (222) configured to respectively couple with corresponding drive outputs (68) of instrument driver (66) of robotic arm (32). While attachment interface (220) with drive inputs (222) are shown on a proximal facing side of proximal housing (212), drive input (222) in another example may alternatively be positioned on a distal facing side of proximal housing (212) for operatively engaging with an alternative arrangement of drive output (68). Shaft assembly (214) of ultrasonic surgical instrument (210) extends through a central bore (224) provided through body (219) of base (218) with an axis substantially parallel to the axes of the drive inputs (222) as discussed briefly above. With shaft assembly (214) positioned at the center of base (218), shaft assembly (214) is coaxial with instrument driver axis (74) when attached and movably received in clearance bore (67). Thus, rotation of rotational assembly (70) causes shaft assembly (214) of ultrasonic surgical instrument (210) to rotate about its own longitudinal axis while clearance bore (67) provides space for translation of shaft assembly (214) during use.

Figures 9A, 9B:
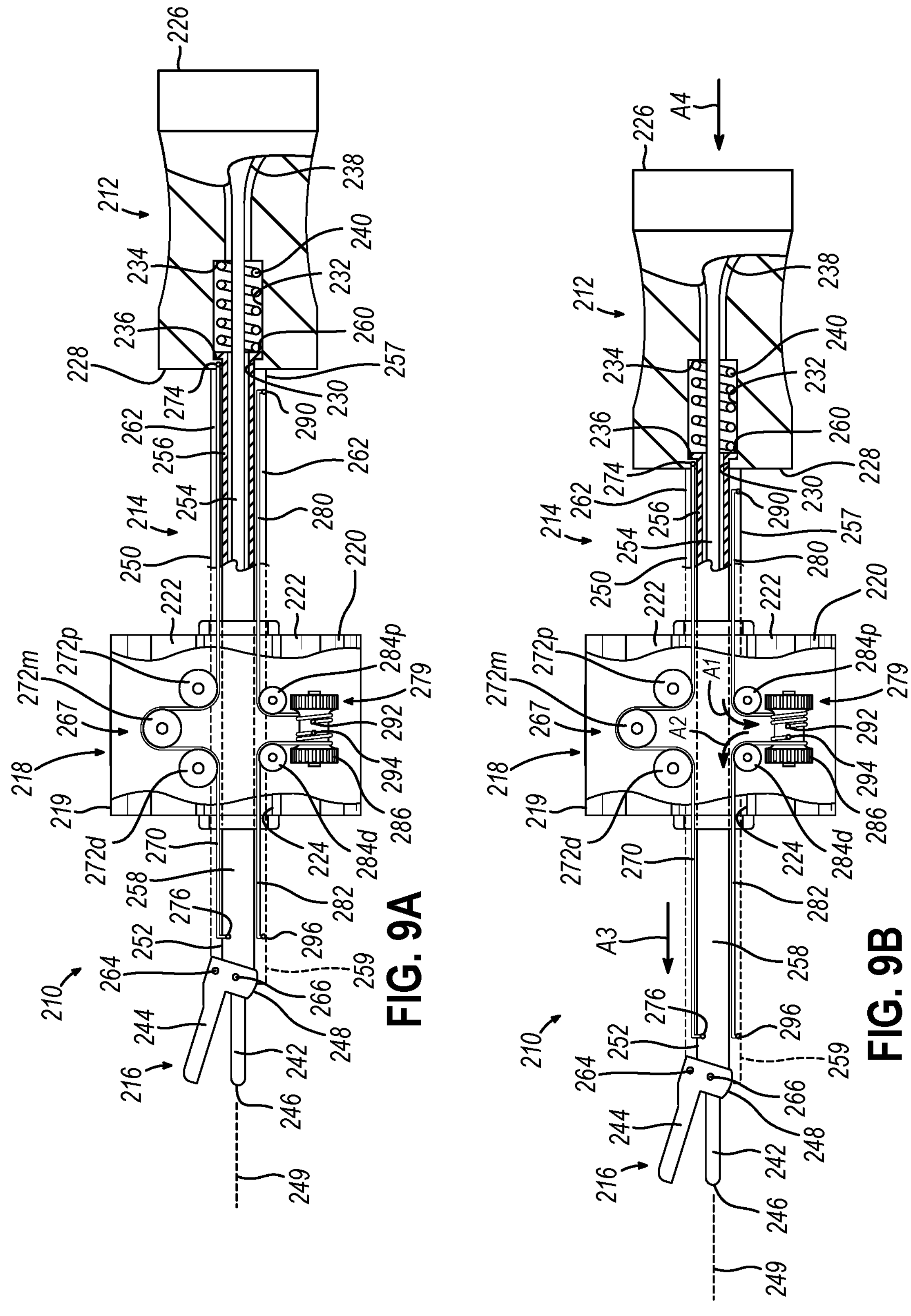
FIG. 9A depicts a schematic, partially cutaway side elevational view of a second exemplary surgical instrument for use with the robotic arm of FIG. 4, showing the surgical instrument in a retracted position with an end effector in an open position.
FIG. 9B depicts the schematic, partially cutaway side elevational view of the surgical instrument similar to FIG. 9A, but in an extended position.

To this end, FIGS. 9A-9D show ultrasonic surgical instrument (210) having the instrument-based insertion architecture as discussed briefly above. Notably, insertion of shaft assembly (214) is grounded at instrument base (218) such that end effector (216) is configured to selectively move longitudinally from a retracted position to an extended position, vice versa, and any desired longitudinal position therebetween. As used herein, the retracted position is shown in FIG. 9A and places end effector (216) relatively close and proximally toward instrument base (218), whereas the extended position is shown in FIG. 9B and places end effector (216) relatively far and distally away from instrument base (218). Insertion into and withdrawal of end effector (216) relative to the patient may thus be facilitated by ultrasonic surgical instrument (210), although it will be appreciated that such insertion into and withdrawal may also occur via robotic arms (see FIG. 5) in one or more examples.

While various features configured to facilitate movement between end effector (216) and drive inputs (222) are described below, such features may additionally or alternatively include pulleys, cables, carriers, such as a kinetic articulating rotating tool (KART), and/or other structures configured to communicate movement along shaft assembly (214). Moreover, while instrument base (218) is configured to operatively connect to instrument driver (66) for driving various features of shaft assembly (214) and/or end effector (216) as discussed below in greater detail, it will be appreciated that alternative examples may operatively connect shaft assembly (214) and/or end effector (216) to an alternative handle assembly (not shown). Such handle assembly (not shown) may include a pistol grip (not shown) in one example, configured to be directly gripped and manipulated by the medical professional for driving various features of shaft assembly (214) and/or end effector (216). The invention is thus not intended to be unnecessarily limited to use with instrument driver (66).

As shown, proximal housing (212) extends between proximal and distal ends (226, 228), and includes a distal opening (230) provided in distal end (228) and communicating with an interior chamber (232) of proximal housing (212). In the example shown, interior chamber (232) defines proximal and distal shoulders (234, 236). An ultrasonic transducer assembly (238) is housed internally within interior chamber (232) and is supported by proximal housing (212). In other configurations, transducer assembly (238) may be provided externally of proximal housing (212). A biasing member in the form of a compression spring (240) (e.g., a coil spring) is also housed internally within interior chamber (232) between proximal and distal shoulders (234, 236), as described below.

End effector (216) of the present example includes an ultrasonic blade (242) and a clamp arm (244) configured to selectively pivot toward and away from ultrasonic blade (242), for clamping tissue therebetween. Ultrasonic blade (242) includes a distal tip (246) and is acoustically coupled with ultrasonic transducer assembly (238), which is configured to drive (i.e., vibrate) ultrasonic blade (242) at ultrasonic frequencies for cutting and/or sealing tissue positioned in contact with ultrasonic blade (242). A clamp pad (not shown) may be secured to a clamping side of clamp arm (244), facing ultrasonic blade (242), for engaging and clamping tissue against a corresponding tissue treatment portion of ultrasonic blade (242) when clamp arm (244) is actuated to its closed position. In the example shown, a pair of arms (248) (one shown) extend transversely from clamp arm (244) for pivotable coupling to a portion of shaft assembly (214).

In this regard, shaft assembly (214) extends along a longitudinal axis (249) and includes an outer tube (250), an inner tube (252) slidably received within outer tube (250), and an ultrasonic waveguide (254) supported within inner tube (252). Inner tube (252) includes a proximal portion (256) and a distal portion (258). In the example shown, proximal portion (256) terminates proximally at a proximal flange (260). Outer tube (250) includes a proximal portion (257) and a distal portion (259), as well as a pair of opposed longitudinal slots (262), the purposes of which are described below.

Figures 9C, 9D:
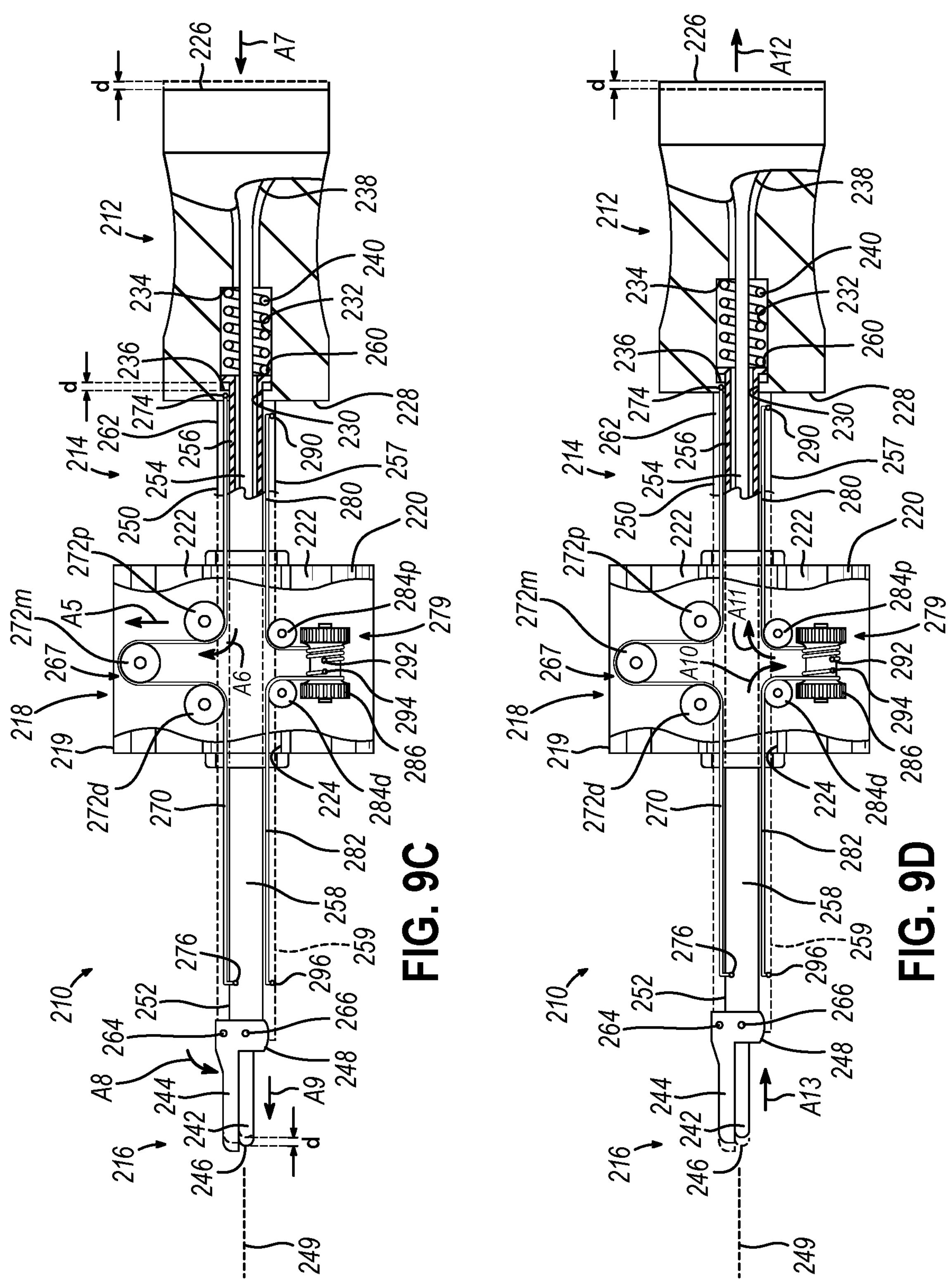
FIG. 9C depicts the schematic, partially cutaway side elevational view of the surgical instrument similar to FIG. 9B, with the end effector of the surgical instrument in a closed position, and further in an over-extended position.
FIG. 9D depicts the schematic, partially cutaway side elevational view of the surgical instrument similar to FIG. 9C, with the end effector returned to the extended position.

Clamp arm (244) of end effector (216) is coupled to distal ends of outer and inner tubes (250, 252). In particular, clamp arm (244) is pivotally secured to a distally projecting tongue (not shown) of outer tube (250) with a first pivot pin (264), and arms (248) are pivotally secured to inner tube (252) with a second pivot pin (266). In the present example, outer tube (250) is longitudinally fixed relative to proximal housing (212) and thus may be referred to as a "static" or "stationary" tube, and inner tube (252) is configured to translate relative to outer tube (250) and proximal housing (212), along the longitudinal axis (249) of shaft assembly (214), and thus may be referred to as a "dynamic" or "movable" tube. As inner tube (252) translates distally relative to outer tube (250), clamp arm (244) pivots about second pivot pin (266) toward its open position (FIGS. 9A and 9B). As inner tube (252) translates proximally relative to outer tube (250), clamp arm (244) pivots about second pivot pin (266) in an opposite direction toward its closed position (FIGS. 9C and 9D). As described below, inner tube (252) is operatively coupled with a closure actuation mechanism (267) for causing translation of inner tube (252) relative to outer tube (250) and proximal housing (212), thereby opening or closing clamp arm (244). In other suitable configurations not shown herein, inner tube (252) may be longitudinally fixed relative to proximal housing (212) and outer tube (250) may be configured to translate relative to proximal housing (212) for moving clamp arm (244) between its open and closed positions. In the example shown, proximal flange (260) of inner tube (252) is received within interior chamber (232) of proximal housing (212), and is configured to selectively abut distal shoulder (236) of proximal housing (212) to limit distal movement of inner tube (252) relative to proximal housing (212). In this regard, compression spring (240) is configured to resiliently bias proximal flange (260) distally relative to proximal housing (212) (e.g., toward distal shoulder (236)) to thereby bias clamp arm (244) toward its open position.

Blade (242) of the present example is operable to vibrate at ultrasonic frequencies in order to effectively cut and/or seal tissue. Blade (242) is positioned at a distal end of an acoustic drivetrain. This acoustic drivetrain includes transducer assembly (238) and acoustic waveguide (254). Transducer assembly (238) is further connected to a generator (not shown) of the acoustic drivetrain. More particularly, transducer assembly (238) is coupled with the generator such that transducer assembly (238) receives electrical power from the generator. Piezoelectric elements (not shown) in transducer assembly (238) convert that electrical power into ultrasonic vibrations. When transducer assembly (238) of the present example is activated, mechanical oscillations are transmitted through waveguide (254) to reach blade (242), thereby providing oscillation of blade (242) at a resonant ultrasonic frequency (e.g., 55.5 kHz). Thus, when tissue is secured between blade (242) and clamp arm (244), the ultrasonic oscillation of blade (242) may simultaneously sever the tissue and denature the proteins in adjacent tissue cells, thereby providing a coagulative effect with relatively little thermal spread.

B. Exemplary Closure Actuation Mechanism

With continuing reference to FIGS. 9A-9D, closure actuation mechanism (267) for actuating end effector of instrument (210) includes a closure cable (270) extending through a set of closure pulleys (272*p*, 272*m*, 272*d*) positioned within instrument base (218). The illustrated set of closure pulleys (272*p*, 272*m*, 272*d*) includes a proximal closure pulley (272*p*), a distal closure pulley (272*d*), and a middle closure pulley (272*m*), each having an axis positioned laterally outwardly relative to central bore (224) and substantially perpendicular to a direction in which the axes of shaft assembly (214), central bore (224), and drive inputs (222) extend. In the example shown, proximal and distal closure pulleys (272*p*, 272*d*) are each longitudinally and laterally fixed relative to body (219) of base (218) such that proximal and distal closure pulleys (272*p*, 272*d*) each extend partially into one of longitudinal slots (262) of outer tube (250), and middle closure pulley (272*m*) is laterally movable (e.g., translatable and/or rotatable) relative to body (219) of base (218) toward or away from central bore (224) (see FIG. 9C). While the various axes of rotations of respective pulleys (272*p*, 272*m*, 272*d*) are described as shown in the present example, such pulleys (272*p*, 272*m*, 272*d*) may be alternatively oriented in other examples, such that the invention is not intended to be unnecessarily limited to the particular orientations of pulleys (272*p*, 272*m*, 272*d*) shown and described herein.

Closure cable (270) extends along an outer surface of inner tube (252), and is grounded to distal end (228) of proximal housing (212) via a proximal closure cable grounding point (274), and is further grounded to distal portion (258) of inner tube (252) via a distal closure cable grounding point (276) positioned distally of instrument base (218). In the example shown, closure cable (270) is slidable within one of longitudinal slots (262) of outer tube (250). In some versions, inner tube (252) may similarly include one or more longitudinal slots (not shown) for accommodating closure cable (270). As shown, closure cable (270) extends through the set of closure pulleys (272*p*, 272*m*, 272*d*) such that closure cable (270) extends at least partially about each of closure pulleys (272*p*, 272*m*, 272*d*). By grounding closure cable (270) to proximal housing (212) and inner tube (252), a total path length of closure cable (270) is kept constant during lateral movement of middle closure pulley (272) relative to body (219) of base (218), while a length of closure cable (270) received within body (219) and a length of closure cable (270) external to body (219) are variable for actuating clamp arm (244).

To this end, in the present version, lateral movement of middle closure pulley (272*m*) relative to body (219) of base (218) affects a length of closure cable (270) received within body (219) by either collecting a portion of closure cable (270) into body (219) or releasing a portion of closure cable (270) from body (219), which also changes an amount of tension in closure cable (270), to thereby actuate clamp arm (244) of end effector (216). For example, a relatively short length of closure cable (270) received within body (219) when middle closure pulley (272*m*) is relatively close to central bore (224) allows clamp arm (244) to be in its open position (FIGS. 9A and 9B), while a relatively long length of closure cable (270) received within body (219) when middle closure pulley (272*m*) is relatively far from central bore (224) places clamp arm (244) in its closed position (FIGS. 9C and 9D). Thus, middle closure pulley (272*m*) may be referred to as an "accumulator pulley." In addition, collecting cable may be referred to as "taking up" cable, whereas releasing cable may be referred to as "giving out" cable.

In this regard, movement of middle closure pulley (272*m*) laterally away from central bore (224) to take up a portion of closure cable (270) increases the length of closure cable (270) received within body (219) and decreases the length of closure cable (270) external to body (219) to thereby cause proximal and distal closure cable grounding points (274, 276) to be pulled toward each other by closure cable (270). This action further causes distal portion (258) of inner tube (252) and distal end (228) of proximal housing (212) to be pulled toward each other. In some cases, this action may be sufficient to overcome the resilient biasing of proximal flange (260) distally relative to proximal housing (212) by compression spring (240). Thus, such movement of middle closure pulley (272*m*) causes inner tube (252) to translate proximally relative to outer tube (250) and proximal housing (212) to thereby pivot clamp arm (244) about second pivot pin (266) toward its closed position.

Conversely, movement of middle closure pulley (272*m*) laterally toward central bore (224) to give out a portion of closure cable (270) decreases the length of closure cable (270) received within body (219) and increase the length of closure cable (270) external to body (219) to thereby allow proximal and distal closure cable grounding points (274, 276) to be pushed away from each other as a result of the resilient biasing of proximal flange (260) distally relative to proximal housing (212) by compression spring (240). This action causes distal portion (258) of inner tube (252) and distal end (228) of proximal housing (212) to be pushed away from each other. Thus, such movement of middle closure pulley (272*m*) causes inner tube (252) to translate distally relative to outer tube (250) and proximal housing (212) to thereby pivot clamp arm (244) about second pivot pin (266) toward its open position.

In some versions, middle closure pulley (272*m*) is operatively coupled to a corresponding drive input (222) of attachment interface (220) for controlling a position of middle closure pulley (272*m*) within body (219). For example, a first predetermined manipulation of the corresponding drive input (222), such as rotary motion thereof in a first direction, moves middle closure pulley (272*m*) laterally toward central bore (224), thereby giving out a portion of closure cable (270) to permit clamp arm (244) to move toward its open position. Conversely, a second predetermined manipulation of the corresponding drive input (222), such as rotary motion thereof in a second direction, moves middle closure pulley (272*m*) laterally away from central bore (224), thereby taking up a portion of closure cable (270) to cause clamp arm (244) to move toward its closed position. It will be appreciated that the position of middle closure pulley (272*m*) within body (219) may be modified by linear and/or rotary motion. To this end, middle closure pulley (272*m*) may be mounted on one or more of a rotary axis, a lever, a gear or track based system to enable adjusting the position of middle closure pulley (272*m*) within body (219). In some versions, closure actuation mechanism (267) may be further configured in accordance with at least some of the teachings of U.S. Pat. No. 10,470,830, entitled "Systems and Methods for Instrument Based Insertion Architectures," issued Nov. 12, 2019, the disclosure of which is incorporated by reference herein.

Closure actuation mechanism (267) advantageously permits free movement of shaft assembly (214) relative to instrument base (218), which includes the set of closure pulleys (272*p*, 272*m*, 272*d*) (which may be accomplished by an insertion actuation mechanism (279) described below), thereby allowing one or more additional cables to be included to permit insertion and retraction of shaft assembly (214) at the same time as actuation of end effector (216) as discussed below in greater detail. For example, it will be appreciated that the closure actuation mechanism (267) enables the lengths of closure cable (270) received within body (219) and external to body (219), as well as the amount of tension in closure cable (270), to be unaffected by insertion and retraction of shaft assembly (214). In this manner, the closure actuation mechanism (267) is considered "decoupled" from the insertion actuation mechanism as described in the present example.

C. Exemplary Insertion Actuation Mechanism

With continuing reference to FIGS. 9A-9D, insertion actuation mechanism (279) for translating shaft assembly (214) of instrument (210) relative to instrument base (218) along an axis of insertion, such as longitudinal axis (249) of the present example, includes proximal and distal insertion cables (280, 282) extending through a set of insertion pulleys (284*p*, 284*d*) to an insertion spool (286) positioned within instrument base (218). The illustrated set of insertion pulleys (284*p*, 284*d*) includes a proximal insertion pulley (284*p*) and a distal insertion pulley (284*d*), each having an axis positioned laterally outwardly relative to central bore (224) (e.g., opposite the set of closure pulleys (272*p*, 272*m*, 272*d*)) and substantially perpendicular to a direction in which the axes of shaft assembly (214), central bore (224), and drive inputs (80) extend. As shown, insertion spool (286) is positioned between proximal and distal insertion pulleys (284*p*, 284*d*), and has an axis substantially parallel to the axes of shaft assembly (214), central bore (224), and drive inputs (80). In the example shown, proximal and distal insertion pulleys (284*p*, 284*d*) and insertion spool (286) are each longitudinally and laterally fixed relative to body of base (218) such that insertion spool (286) is positioned laterally outwardly from proximal and distal insertion pulleys (284*p*, 284*d*), and such that proximal and distal insertion pulleys (284*p*, 284*d*) each extend partially into one of longitudinal slots (262) of outer tube (250) (e.g., opposite that which receives proximal and distal closure pulleys (272*p*, 272*d*)). While the various axes of rotations of respective pulleys (284*p*, 284*d*) are described as shown in the present example, such pulleys (284*p*, 284*d*) may be alternatively oriented in other examples, such that the invention is not intended to be unnecessarily limited to the particular orientations of pulleys (284*p*, 284*d*) shown and described herein.

Proximal insertion cable (280) extends along an outer surface of inner tube (252) (e.g., laterally opposite a proximal portion of closure cable (270)), and is grounded to proximal portion (257) of outer tube (250) via a proximal, proximal insertion cable grounding point (290) positioned proximally of instrument base (218), and is further grounded to insertion spool (286) via a distal, proximal insertion cable grounding point (292). Likewise, distal insertion cable (282) extends along an outer surface of inner tube (252) (e.g., laterally opposite a distal portion of closure cable (270)), and is grounded to insertion spool (286) via a proximal, distal insertion cable grounding point (294), and is further grounded to distal portion (259) of outer tube (250) via a distal, distal insertion cable grounding point (296) positioned distally of instrument base (218). In the example shown, proximal and distal insertion cables (280, 282) are each received within one of longitudinal slots (262) of outer tube (250) (e.g., laterally opposite that which receives closure cable (270)). In some versions, inner tube (252) may similarly include one or more longitudinal slots (not shown) for accommodating at least one of proximal or distal insertion cables (280, 282). As shown, proximal insertion cable (280) extends at least partially about proximal insertion pulley (284*p*) and is at least partially wound onto insertion spool (286). Similarly, distal insertion cable (282) extends at least partially about distal insertion pulley (284*d*) and is at least partially wound onto insertion spool (286). By grounding proximal and distal insertion cables (280, 282) to insertion spool (286), path lengths of each of proximal and distal insertion cables (280, 282) and, more particularly, lengths of proximal and distal insertion cables (280, 282) external to body (219), may be variable.

In the present version, rotation of insertion spool (286) about its axis relative to body of base (218) affects path lengths of proximal and distal insertion cables (280, 282) either by winding, spooling, or "paying in" a portion of proximal insertion cable (280) and unwinding, unspooling, or "paying out" a portion of distal insertion cable (282), or by paying in a portion of distal insertion cable (282) and paying out a portion of proximal insertion cable (280), which also adjusts tension in insertion cables (280, 282), to thereby translate shaft assembly (214) relative to base (218). For example, a relatively short length of distal insertion cable (282) is external to body (219) and a relatively long length of proximal insertion cable (280) is external to body (219) when insertion spool (286) is in a first rotational position or angular orientation relative to its axis to place shaft assembly (214) in its retracted position (FIG. 9A). Furthermore, a relatively long length of distal insertion cable (282) is external to body (219) and a relatively short length of proximal insertion cable (280) is external to body (219) when insertion spool (286) is in a second rotational position or angular orientation relative to its axis to place shaft assembly (214) in its extended position (FIG. 9B).

In this regard, rotation of insertion spool (286) about its axis in a first (e.g., clockwise) direction to pay in a portion of proximal insertion cable (280) and pay out a portion of distal insertion cable (282) increases the length of distal insertion cable (282) external to body (219) and decreases the length of proximal insertion cable (280) external to body (219). Such length adjustments thereby cause proximal, proximal insertion cable grounding point (290) to be pulled toward distal, proximal insertion cable grounding point (292) by proximal insertion cable (280), and allow distal, distal insertion cable grounding point (296) to be pushed away from proximal, distal insertion cable grounding point (294). This action causes proximal portion (257) of outer tube (250) to be pulled distally toward insertion spool (286) by proximal insertion cable (280). In some cases, a rigid connection between outer tube (250) and proximal housing (212) causes proximal housing (212) to be pulled distally together with proximal portion (257) of outer tube (250) toward insertion spool (286) by proximal insertion cable (280), and engagement between proximal flange (260) of inner tube (252) and compression spring (240) within proximal housing (212) causes proximal portion (256) of inner tube (252) to be pushed distally toward insertion spool (286) during pulling of proximal portion (257) of outer tube (250) and proximal housing (212) toward insertion spool (286) by proximal insertion cable (280). For example, the resilient biasing of proximal flange (260) distally by compression spring (240) may assist in pushing proximal portion (256) of inner tube (252) distally toward insertion spool (286) during such pulling of proximal portion (257) of outer tube (250) and proximal housing (212). Thus, such rotation of insertion spool (286) causes shaft assembly (214) to translate distally relative to base (218) to thereby extend end effector (216) toward its extended position.

Conversely, rotation of insertion spool (286) about its axis in a second (e.g., counterclockwise) direction to pay in a portion of distal insertion cable (282) and pay out a portion of proximal insertion cable (280) increases the length of proximal insertion cable (280) external to body (219) and decreases the length of distal insertion cable (282) external to body (219) to thereby cause distal, distal insertion cable grounding point (296) to be pulled toward proximal, distal insertion cable grounding point (294) by distal insertion cable (282), and allow proximal, proximal insertion cable grounding point (290) to be pushed away from distal, proximal insertion cable grounding point (292). This action causes distal portion (259) of outer tube (250) to be pulled proximally toward insertion spool (286) by distal insertion cable (282). In some cases, the rigid connection between outer tube (250) and proximal housing (212) causes proximal housing (212) to be pushed proximally away from insertion spool (286) during pulling of distal portion (259) of outer tube (250) proximally toward insertion spool (286) by distal insertion cable (282), and abutment between proximal flange (260) of inner tube (252) and distal shoulder (236) of proximal housing (212) causes proximal portion (256) of inner tube (252) to be pulled proximally together with proximal housing (212) away from insertion spool (286) during pulling of distal portion (259) of outer tube (250) proximally toward insertion spool (286) by distal insertion cable (282). In addition, or alternatively, the amount of tension in closure cable (270) may remain constant during pulling of distal portion (259) of outer tube (250) proximally toward insertion spool (286) by distal insertion cable (282), such that distal closure cable grounding point (276) is pulled proximally via closure cable (270) by the same distance that proximal closure cable grounding point (274) is pushed proximally by virtue of its attachment to proximal housing (212), to thereby cause distal portion (258) of inner tube (252) to be pulled proximally toward insertion spool (286) during pulling of distal portion (259) of outer tube (250) proximally toward insertion spool (286) by distal insertion cable (282). Thus, such rotation of insertion spool (286) causes shaft assembly (214) to translate proximally relative to base (218) to thereby retract end effector (216) toward its retracted position.

In some versions, insertion spool (286) is operatively coupled to a corresponding drive input (222) of attachment interface (220) for controlling a rotational position of insertion spool (286) about its axis within body (219). For example, a first predetermined manipulation of the corresponding drive input (222), such as rotary motion thereof in a first direction, rotates insertion spool (286) in a clockwise direction, thereby paying in a portion of proximal insertion cable (280) and paying out a portion of distal insertion cable (282) to cause shaft assembly (214) to move toward its extended position. Conversely, a second predetermined manipulation of the corresponding drive input (222), such as rotary motion thereof in a second direction, rotates insertion spool (286) in a counterclockwise direction, thereby paying in a portion of distal insertion cable (282) and paying out a portion of proximal insertion cable (280) to cause shaft assembly (214) to move toward its retracted position. It will be appreciated that the rotational position of insertion spool (286) within body (219) may be modified by linear and/or rotary motion. In some versions, insertion actuation mechanism (279) may be further configured in accordance with at least some of the teachings of U.S. Pat. No. 10,470,830, entitled "Systems and Methods for Instrument Based Insertion Architectures," issued Nov. 12, 2019.

D. Operation of Second Exemplary Ultrasonic Surgical Instrument

With continuing reference to FIGS. 9A-9D, during operation in one example, shaft assembly (214) is initially in a retracted position and clamp arm (244) is initially in an open position, as shown in FIG. 9A. In some versions, instrument base (218) may be attached to instrument driver (66) of robotic arm (32) with drive inputs (222) of attachment interface (220) respectively coupled with corresponding drive outputs (68). In any event, body (219) of instrument base (218) defines a fixed reference relative to the various movements of other components of instrument (210) described below.

In order to insert end effector (216) (e.g., into an access point of a patient), insertion spool (286) is rotated about its axis in a clockwise direction, such as via a corresponding drive input (222), to pay in a portion of proximal insertion cable (280), as indicated by an arrow (A1) in FIG. 9B, and pay out a portion of distal insertion cable (282), as indicated by an arrow (A2) in FIG. 9B. This rotation of insertion spool (286) causes outer tube (250) to translate distally relative to body (219) of base (218), as indicated by an arrow (A3) in FIG. 9B. Proximal housing (212) and inner tube (252) translate distally together with outer tube (250) relative to body (219) of base (218) as described above, as indicated by an arrow (A4) in FIG. 9B. Thus, proximal housing (212), shaft assembly (214), and end effector (216) collectively translate distally relative to body (219) of base (218) from the retracted position shown in FIG. 9A to the extended position shown in FIG. 9B. It will be appreciated that the length of closure cable (270) within base (218) remains constant during such translation, such that clamp arm (244) remains in its open position. In some versions, distal tip (246) of blade (242) is positioned at a predetermined target location when end effector (216) is in its extended position. For example, the target location may be at or near a targeted tissue to be treated by blade (242).

In order to close clamp arm (244) of end effector (216), middle closure pulley (272*m*) is be moved laterally away from central bore (224), as indicated by an arrow (A5) in FIG. 9C, such as via a corresponding drive input (222), to take up a portion of closure cable (270), as indicated by an arrow (A6) in FIG. 9C. This movement of middle closure pulley (272*m*) causes inner tube (252) to translate proximally relative to outer tube (250) and proximal housing (212). In some versions, this movement of middle closure pulley (272*m*) causes outer tube (250) and proximal housing (212) to translate distally relative to inner tube (252) by a distance (d), as indicated by an arrow (A7) in FIG. 9C to thereby pivot clamp arm (244) about second pivot pin (266) toward its closed position, as indicated by an arrow (A8) in FIG. 9C. Thus, clamp arm (244) pivots from the open position shown in FIG. 9B to the closed position shown in FIG. 9C.

In some versions, the lateral movement of middle closure pulley (272*m*) away from central bore (224) for closing clamp arm (244) causes outer tube (250) and proximal housing (212) to translate distally relative to body (219) of base (218), such that proximal housing (212) translates distally from its extended position shown in FIG. 9B to an over-extended position shown in FIG. 9C by distance (d). As a result, blade (242) also translates distally from its extended position shown in FIG. 9B to an over-extended position shown in FIG. 9C by distance (d), as indicated by an arrow (A9) in FIG. 9C. Thus, closure of clamp arm (244) causes distal tip (246) of blade (242) to travel distally beyond its target location by distance (d).

In order to return blade (242) to its extended position for positioning distal tip (246) of blade (242) at the predetermined target location, insertion spool (286) rotates about its axis in a counterclockwise direction, such as via a corresponding drive input (222), to pay in a portion of distal insertion cable (282), as indicated by an arrow (A10) in FIG. 9D, and pay out a portion of proximal insertion cable (280), as indicated by an arrow (A11) in FIG. 9D. The amount of rotation of insertion spool (286) may be selected to pay in and out sufficient portions of distal insertion cable (282) and proximal insertion cable (280), respectively, to cause outer tube (250) to translate proximally relative to body (219) of base (218) by distance (d). In this respect, proximal housing (212) and inner tube (252) translate proximally together with outer tube (250) relative to body (219) of base (218) as described above by distance (d), such that proximal housing (212) translates proximally from its over-extended position shown in FIG. 9C to its extended position shown in FIG. 9D, as indicated by an arrow (A12) in FIG. 9D, while maintaining clamp arm (244) in its closed position. As a result, blade (242) also translates proximally from its over-extended position shown in FIG. 9C to its extended position shown in FIG. 9D, as indicated by an arrow (A13) in FIG. 9D. In this manner, insertion actuation mechanism (279) is configured to compensate for over-extension of blade (242) that may be caused by closure of clamp arm (244).

In order to open clamp arm (244) of end effector (216), middle closure pulley (272*m*) is moved laterally toward central bore (224), such as via a corresponding drive input (222), to give out a portion of closure cable (270). This movement of middle closure pulley (272*m*) causes inner tube (252) to translate distally relative to outer tube (250) and proximal housing (212) via compression spring (240), and/or causes outer tube (250) and proximal housing (212) to translate proximally relative to inner tube (252) (e.g., by distance (d)) via compression spring (240) to thereby pivot clamp arm (244) about second pivot pin (266) toward its open position. Thus, clamp arm (244) pivots from the closed position shown in FIG. 9D to the open position shown in FIG. 9B.

In order to retract end effector (216) (e.g., out of the access point of the patient), insertion spool (286) rotates about its axis in a counterclockwise direction, such as via a corresponding drive input (222), to pay in a portion of distal insertion cable (282) and pay out a portion of proximal insertion cable (280). This rotation of insertion spool causes outer tube (250) to translate proximally relative to body (219) of base (218). Proximal housing (212) and inner tube (252) translate proximally together with outer tube (250) relative to body of base (218) as described above. Thus, proximal housing (212), shaft assembly (214), and end effector (216) collectively translate proximally relative to body (219) of base (218) from the extended position shown in FIG. 9B to the retracted position shown in FIG. 9A.

E. Automatic Compensation of Blade Over-Extension

Figure 10:
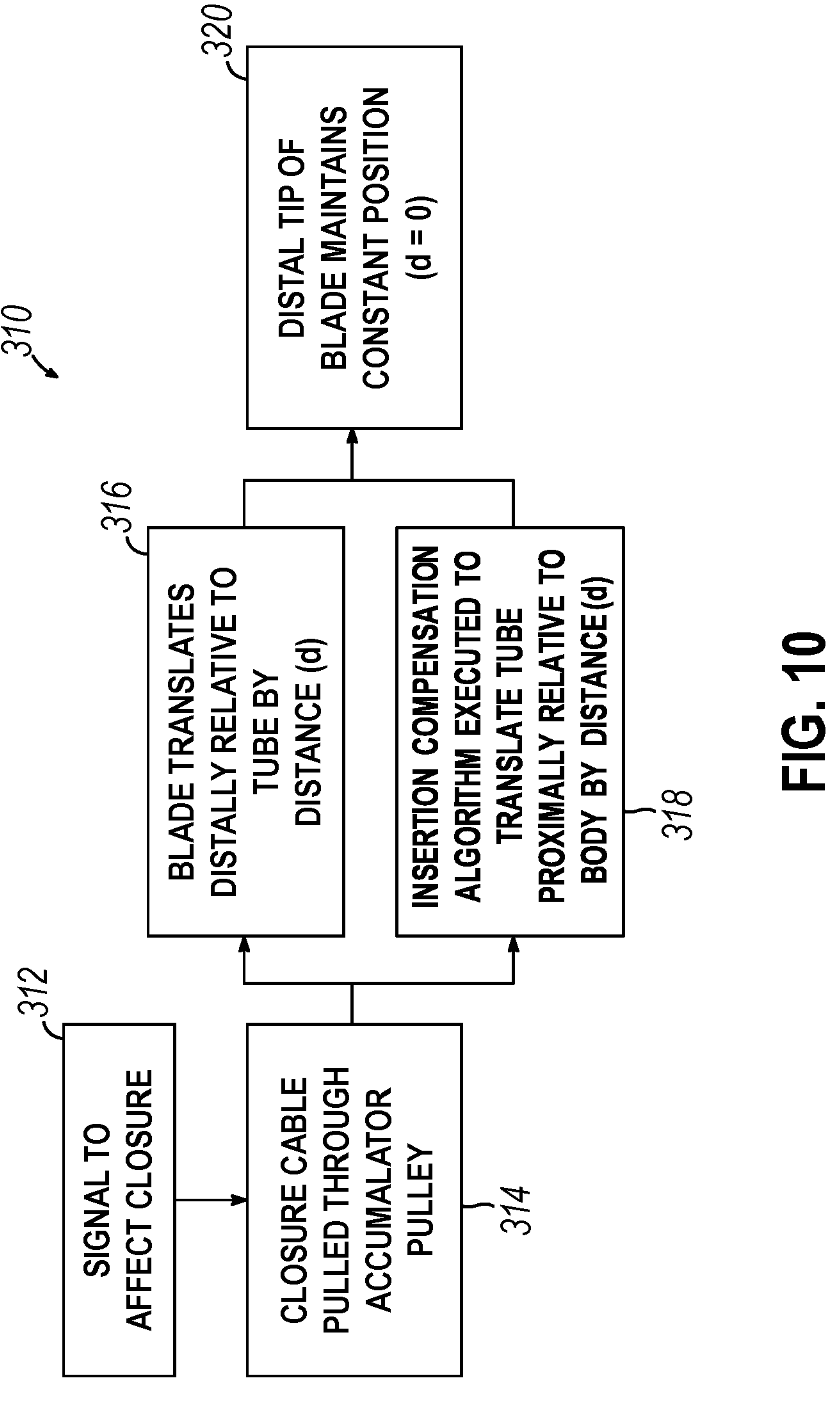
FIG. 10 depicts a flowchart of a method for automatically compensating for the over-extension of the end effector of FIGS. 9A-9D due to closure of the end effector.

In some instances, it may be desirable to reduce, or even eliminate, the over-extension of blade (242) of ultrasonic surgical instrument (210) caused by movement of clamp arm (244) toward its closed position. FIG. 10 shows an example of a method (310) for automatically compensating for this over-extension of blade (242).

Method (310) begins with step (312), which may follow insertion of end effector (216) to its extended position (see FIG. 9B). In step (312), an input controller (not shown) sends a signal to instrument driver (66) for laterally moving middle closure pulley (272*m*) to affect closure of clamp arm (244), and method (310) then proceeds to step (314). In step (314), a portion of closure cable (270) is taken up by middle closure pulley (272*m*), and method (310) then proceeds to steps (316, 318). In step (316), blade (242) translates distally relative to inner tube (252) by distance (d) as a result of outer tube (250) and proximal housing (212) translating distally relative to inner tube (252) by distance (d) to close clamp arm (244). In step (318), the input controller executes an insertion compensation algorithm, which includes calculating a desired amount of rotation of insertion spool (286) for translating inner tube (252) (e.g., together with outer tube (250) and proximal housing (212)) proximally relative to body (219) of instrument base (218) by distance (d), and sending a signal to instrument driver (66) for rotating insertion spool (286) by the desired amount of rotation to translate inner tube (252) (e.g., together with outer tube (250) and proximal housing (212)) proximally relative to body (219) by distance (d). As shown, steps (316, 318) are performed substantially simultaneously. For example, step (316) is performed during performance of step (318), and vice versa. Thus, method (310) proceeds from steps (316, 318) to step (320), wherein blade (242) maintains a constant extended position such that distal tip (246) of blade (242) is maintained at the target location without traveling distally therefrom during closure of clamp arm (244).

While method (310) is described above in connection with ultrasonic surgical instrument (210), method (310) may be applied to an endocutter, such as a dual-pivot endocutter.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument comprising: (a) a shaft assembly including a waveguide configured to connect to an ultrasonic transducer; (b) an end effector arranged at a distal end of the shaft assembly, wherein the end effector includes: (i) an ultrasonic blade acoustically coupled with the waveguide and configured to be driven by the waveguide with ultrasonic energy, and (ii) a clamp arm movably secured relative to the ultrasonic blade and configured to move from an open position configured to receive a tissue toward a closed position configured to clamp the tissue against the ultrasonic blade; (c) a base translatably coupled to shaft assembly such that the shaft assembly is configured to move from a proximal position toward a distal position relative to the base, wherein the base includes: (i) a first mechanical input, and (ii) a second mechanical input; (d) a closure actuation mechanism operatively connected between the first mechanical input and the clamp arm and configured to actuate the clamp arm from the open position toward the closed position upon selective drive of the first mechanical input; and (e) an insertion actuation mechanism operatively connected between the second mechanical input and the shaft assembly and configured to actuate the shaft assembly from the proximal position toward the distal position upon selective drive of the second mechanical input for insertion of the end effector.

Example 2

The ultrasonic surgical instrument of Example 1, wherein the closure actuation mechanism is decoupled from the insertion actuation mechanism such that the closure and insertion actuation mechanisms are configured to be independently driven relative to each other via the first and second mechanical inputs.

Example 3

The ultrasonic surgical instrument of Example 2, wherein at least a portion of the closure actuation mechanism is secured relative to the base, and wherein at least a portion of the insertion actuation mechanism is secured relative to the base.

Example 4

The ultrasonic surgical instrument of any one or more of Examples 1 through 3, further comprising: (a) a proximal housing; and (b) the ultrasonic transducer, wherein the ultrasonic transducer is supported by the proximal housing, wherein the shaft assembly further includes: (i) a static tube fixed against movement relative to the proximal housing, and (ii) a dynamic tube translatable relative to the static tube, wherein the waveguide is received within the dynamic tube, wherein the dynamic tube is configured to actuate the clamp arm upon translation of the dynamic tube relative to the static tube, and wherein the dynamic tube is operatively connected to the closure actuation mechanism to actuate the clamp arm from the open position toward the closed position upon selective drive of the first mechanical input.

Example 5

The ultrasonic surgical instrument of Example 4, wherein the closure actuation mechanism includes a closure cable that extends through a set of closure pulleys, wherein manipulation of at least one pulley of the set of closure pulleys via the first mechanical input causes a change of length of the closure cable within the base, thereby causing translation of the dynamic tube relative to the static tube.

Example 6

The ultrasonic surgical instrument of Example 5, wherein the dynamic tube includes a proximal portion and a distal portion, wherein the closure cable of the closure actuation mechanism extends from the proximal housing, through the set of closure pulleys, to the distal portion of the dynamic tube.

Example 7

The ultrasonic surgical instrument of claim 6, wherein manipulation of the at least one pulley of the set of closure pulleys to cause a change of length of the closure cable within the base comprises linear or rotary motion of the at least one pulley.

Example 8

The ultrasonic surgical instrument of Example 7, wherein the change of length of the closure cable within the base to cause translation of the dynamic tube relative to the static tube is not affected by the insertion actuation mechanism that translates the shaft assembly relative to the base.

Example 9

The ultrasonic surgical instrument of any one or more of Examples 4 through 8, wherein the dynamic tube is biased distally relative to the proximal housing.

Example 10

The ultrasonic surgical instrument of any one or more of Examples 4 through 9, wherein the static tube includes an outer tube, wherein the dynamic tube includes an inner tube.

Example 11

The surgical instrument of any one or more of Examples 4 through 10, wherein the closure actuation mechanism is operatively connected to a distal end of the dynamic tube, wherein the insertion actuation mechanism is operatively connected to a distal end of the static tube.

Example 12

The ultrasonic surgical instrument of any one or more of Examples 1 through 11, wherein the insertion actuation mechanism includes at least one insertion cable that engages a spool, wherein manipulation of the spool via the second mechanical input causes the shaft assembly to translate relative to the base.

Example 13

The ultrasonic surgical instrument of Example 12, wherein the at least one insertion cable includes a proximal insertion cable and a distal insertion cable.

Example 14

The ultrasonic surgical instrument of Example 13, wherein the shaft assembly further includes an static tube and a dynamic tube, wherein the static tube includes a proximal portion and a distal portion, wherein the proximal insertion cable extends from the proximal portion of the static tube to the spool, wherein the distal insertion cable extends from the distal portion of the static tube to the spool.

Example 15

The ultrasonic surgical instrument of any one or more of Examples 12 through 14, wherein rotation of the second mechanical input causes rotation of the spool thereby causing translation of the shaft assembly relative to the base.

Example 16

An ultrasonic surgical instrument comprising: (a) a proximal housing; (b) a shaft assembly extending distally from the proximal housing, wherein the shaft assembly comprises: (i) a static tube fixed against movement relative to the proximal housing, and (ii) a dynamic tube translatable relative to the static tube; (c) an ultrasonic transducer supported by the proximal housing; (d) a waveguide acoustically coupled with the ultrasonic transducer and extending distally through the dynamic tube of the shaft assembly; (e) an end effector arranged at a distal end of the shaft assembly, wherein the end effector comprises: (i) an ultrasonic blade acoustically coupled with the waveguide, wherein the ultrasonic transducer is operable to drive the waveguide and the ultrasonic blade with ultrasonic energy, and (ii) a clamp arm movable relative to the ultrasonic blade for clamping tissue therebetween, wherein the dynamic tube is operable to translate relative to the static tube to actuate the clamp arm relative to the ultrasonic blade; and (f) a base translatably coupled to shaft assembly, wherein the base comprises: (i) a first mechanical input configured to cause the dynamic tube to translate relative to the static tube to actuate the clamp arm relative to the ultrasonic blade, and (ii) a second mechanical input configured to cause the shaft assembly to translate relative to the base.

Example 17

The ultrasonic surgical instrument of Example 16, further comprising: (a) a closure actuation mechanism, wherein the closure actuation mechanism includes a closure cable that extends through a set of closure pulleys, wherein manipulation of at least one pulley of the set of closure pulleys causes a change of length of the closure cable within the base, thereby causing translation of the dynamic tube relative to the static tube; and (b) an insertion actuation mechanism, wherein the insertion actuation mechanism includes at least one insertion cable that engages a spool, wherein manipulation of the spool causes the shaft assembly to translate relative to the base.

Example 18

A method of using an ultrasonic surgical instrument including a shaft assembly having a dynamic tube and a static tube, an end effector having an ultrasonic blade and a clamp arm, and a base, the method comprising: (a) translating the shaft assembly relative to the base, wherein the act of translating the shaft assembly relative to the base includes rotating a spool to pay in one of a proximal insertion cable or a distal insertion cable and to pay out the other of the proximal or distal insertion cables; and (b) actuating the clamp arm relative to the ultrasonic blade, wherein the act of actuating the clamp arm relative to the ultrasonic blade includes manipulating at least one closure pulley to cause a change of length of a closure cable within the base to thereby translate the dynamic tube relative to the static tube.

Example 19

The method of Example 18, wherein the act of translating the shaft assembly relative to the base includes maintaining a constant length of the closure cable within the base.

Example 20

The method of any one or more of Examples 18 through 19, wherein the act of actuating the clamp arm relative to the ultrasonic blade includes translating the ultrasonic blade distally relative to the dynamic tube by a distance, the method further comprising translating the dynamic tube proximally relative to the base by the distance.

Example 21

A surgical instrument comprising: (a) a shaft assembly, wherein the shaft assembly comprises: (i) an outer tube, and (ii) an inner tube translatable relative to the outer tube; (b) an ultrasonic transducer; (c) a waveguide acoustically coupled with the ultrasonic transducer and extending distally through the inner tube of the shaft assembly; (d) an end effector arranged at a distal end of the shaft assembly, wherein the end effector comprises: (i) an ultrasonic blade acoustically coupled with the waveguide, wherein the ultrasonic transducer is operable to drive the waveguide and the ultrasonic blade with ultrasonic energy, and (ii) a clamp arm movable relative to the ultrasonic blade for clamping tissue therebetween, wherein the inner tube is operable to translate relative to the outer tube to actuate the clamp arm relative to the ultrasonic blade; (e) a base translatably coupled to the shaft assembly; and (f) a closure actuation mechanism, wherein the closure actuation mechanism includes a closure cable that extends through a set of closure pulleys, wherein manipulation of at least one pulley of the set of closure pulleys causes a change of length of the closure cable within the base, thereby causing translation of the inner tube relative to the outer tube.

Example 22

The surgical instrument of Example 21, further comprising an insertion actuation mechanism, wherein the insertion actuation mechanism includes at least one insertion cable that engages a spool, wherein manipulation of the spool causes the shaft assembly to translate relative to the base.

IV. MISCELLANEOUS

Any one or more of the teaching, expressions, embodiments, examples, etc. described herein may be combined with any one or more of the teachings, expressions, embodiments, examples, etc. described in U.S. patent application Ser. No. 17/077,067, entitled "Surgical Instrument and Carrier KART Supporting Ultrasonic Transducer," filed on Oct. 22, 2020, published as U.S. Pub. No. 2022/0125465 on Apr. 28, 2022; U.S. patent application Ser. No. 17/077,086, entitled "Carrier KART and Jaw Closure of an Ultrasonic Surgical Instrument," filed on Oct. 22, 2020, published as U.S. Pub. No. 2022/0125466 on Apr. 28, 2022; U.S. patent application Ser. No. 17/077,130, entitled "Surgical Instrument with Clamping Sensor Feedback and Related Methods," filed on Oct. 22, 2020, published as U.S. Pub. No. 2022/0125469 on Apr. 28, 2022; U.S. patent application Ser. No. 17/077,136, entitled "Surgical Instrument with Non-clamping Sensor Feedback and Related Methods," filed on Oct. 22, 2020, published as U.S. Pub. No. 2022/0125470 on Apr. 28, 2022; U.S. patent application Ser. No. 17/077,250, entitled "Ultrasonic Surgical Instrument with a Carrier KART and Reusable Stage," filed on Oct. 22, 2020, published as U.S. Pub. 2022/0125472 on Apr. 28, 2022; U.S. patent application Ser. No. 17/077,373, entitled "Surgical Instrument with a Carrier KART and Various Communication Cable Arrangements," filed on Oct. 22, 2020, published as U.S. Pub. 2022/0125473 on Apr. 28, 2022; U.S. patent application Ser. No. 17/077,139, entitled "Ultrasonic Surgical Instrument with a Fixed Transducer Grounding," filed on Oct. 22, 2020, published as U.S. Pub. 2022/0125471 on Apr. 28, 2022; U.S. patent application Ser. No. 17/077,146, entitled "Ultrasonic Surgical Instrument with a Shaft Assembly and Elongated Waveguide Support Arrangement," filed on Oct. 22, 2020, published as U.S. Pub. 2022/0125460 on Apr. 28, 2022; U.S. patent application Ser. No. 17/077,152, entitled "Damping Rings for an Ultrasonic Surgical Instrument," filed on Oct. 22, 2020, issued as U.S. Pat. No. 11,806,037 on Nov. 7, 2023; U.S. patent application Ser. No. 17/076,956, entitled "Surgical Instrument with an Articulatable Shaft Assembly and Dual End Effector Roll," filed on Oct. 22, 2020, published as U.S. pub. No. 2022/0125463 on Apr. 28, 2022; U.S. patent application Ser. No. 17/076,959, entitled "Ultrasonic Surgical Instrument with a Distally Grounded Acoustic Waveguide," filed on Oct. 22, 2020, published as U.S. Pub. No. 2022/0125464 on Apr. 28, 2022; and/or U.S. patent application Ser. No. 17/077,098, entitled "Ultrasonic Surgical Instrument with a Multiplanar Articulation Joint," filed on Oct. 22, 2020, published as U.S. Pub. No. 2022/0125467 on Apr. 28, 2022. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
(a) a shaft assembly including a waveguide configured to connect to an ultrasonic transducer;
(b) an end effector arranged at a distal end of the shaft assembly, wherein the end effector includes:
(i) an ultrasonic blade acoustically coupled with the waveguide and configured to be driven by the waveguide with ultrasonic energy, and
(ii) a clamp arm movably secured relative to the ultrasonic blade and configured to move from an open position configured to receive a tissue toward a closed position configured to clamp the tissue against the ultrasonic blade;
(c) a base translatably coupled to the shaft assembly such that the shaft assembly is configured to move from a proximal position toward a distal position relative to the base, wherein the base includes:
(i) a first mechanical input, and
(ii) a second mechanical input;
(d) a closure actuator operatively connected between the first mechanical input and the clamp arm and configured to actuate the clamp arm from the open position toward the closed position upon selective drive of the first mechanical input; and
(e) an insertion actuator operatively connected between the second mechanical input and the shaft assembly and configured to actuate the shaft assembly from the proximal position toward the distal position upon selective drive of the second mechanical input for insertion of the end effector,
wherein the clamp arm is configured to translate distally relative to the base to a clamp arm over-extended position when the clamp arm moves from the open position to the closed position.

2. The ultrasonic surgical instrument of claim 1, wherein the clamp arm is configured to translate proximally relative to the base from the clamp arm over-extended position to a clamp arm extended position while the clamp arm is in the closed position.

3. The ultrasonic surgical instrument of claim 1, further comprising a proximal housing and a dynamic tube, wherein the proximal housing is positioned proximally relative to the base, and wherein the dynamic tube is operatively connected to the closure actuator to actuate the clamp arm from the open position toward the closed position upon selective drive of the first mechanical input.

4. The ultrasonic surgical instrument of claim 3, wherein the proximal housing is configured to translate distally relative to the base to a proximal housing over-extended position when the clamp arm moves from the open position to the closed position.

5. The ultrasonic surgical instrument of claim 4, wherein the proximal housing is configured to translate proximally relative to the base from the proximal housing over-extended position to a proximal housing extended position while the clamp arm is in the closed position.

6. The ultrasonic surgical instrument of claim 3, wherein the ultrasonic transducer is supported by the proximal housing.

7. The ultrasonic surgical instrument of claim 3, wherein the shaft assembly further includes:
(i) a static tube fixed against movement relative to the proximal housing, and
(ii) a dynamic tube translatable relative to the static tube,
wherein the waveguide is received within the dynamic tube, wherein the dynamic tube is configured to actuate the clamp arm upon translation of the dynamic tube relative to the static tube, and
wherein the dynamic tube is operatively connected to the closure actuator to actuate the clamp arm from the open position toward the closed position upon selective drive of the first mechanical input.

8. An ultrasonic surgical instrument, comprising:
(a) a proximal housing;
(b) a shaft assembly extending distally from the proximal housing, wherein the shaft assembly comprises:
(i) a static tube fixed against movement relative to the proximal housing, and
(ii) a dynamic tube translatable relative to the static tube;
(c) an ultrasonic transducer supported by the proximal housing;
(d) a waveguide acoustically coupled with the ultrasonic transducer and extending distally through the dynamic tube of the shaft assembly;
(e) an end effector arranged at a distal end of the shaft assembly, wherein the end effector comprises:
(i) an ultrasonic blade acoustically coupled with the waveguide, wherein the ultrasonic transducer is configured to drive the waveguide and the ultrasonic blade with ultrasonic energy, and
(ii) a clamp arm movable relative to the ultrasonic blade from an open position to a closed position, wherein the dynamic tube is configured to translate relative to the static tube to actuate the clamp arm relative to the ultrasonic blade; and
(f) a base translatably coupled to the shaft assembly, wherein the base comprises:
(i) a first mechanical input configured to cause the dynamic tube to translate relative to the static tube to actuate the clamp arm relative to the ultrasonic blade, and
(ii) a second mechanical input configured to cause the shaft assembly to translate relative to the base,
wherein at least one of the dynamic tube or the proximal housing translates such that:
the dynamic tube is configured to translate distally relative to the static tube when actuating the clamp arm relative to the ultrasonic blade from the open position to the closed position,
the dynamic tube is configured to translate proximally relative to the static tube while the clamp arm is in the closed position, or
the proximal housing is configured to translate distally to a proximal housing over-extended position when the clamp arm moves from the open position to the closed position.

9. The ultrasonic surgical instrument of claim 8, further comprising:
(a) a closure actuator, wherein the closure actuator includes a closure cable that extends through a set of closure pulleys, wherein manipulation of at least one pulley of the set of closure pulleys causes a change of length of the closure cable within the base, thereby causing translation of the dynamic tube relative to the static tube; and (b) an insertion actuator, wherein the insertion actuator includes at least one insertion cable that engages a spool, wherein manipulation of the spool causes the shaft assembly to translate relative to the base.

10. The ultrasonic surgical instrument of claim 8, wherein the dynamic tube is configured to translate distally relative to the static tube when actuating the clamp arm relative to the ultrasonic blade from the open position to the closed position.

11. The ultrasonic surgical instrument of claim 8, wherein the dynamic tube is configured to translate proximally relative to the static tube while the clamp arm is in the closed position.

12. The ultrasonic surgical instrument of claim 8, wherein the proximal housing is configured to translate distally to a proximal housing over-extended position when the clamp arm moves from the open position to the closed position.

13. The ultrasonic surgical instrument of claim 12, wherein the proximal housing is configured to translate proximally while the clamp arm is in the closed position.

14. A method of using an ultrasonic surgical instrument including a shaft assembly having a dynamic tube and a static tube, an end effector having an ultrasonic blade and a clamp arm, and a base, the method comprising:

(a) translating the shaft assembly relative to the base, wherein the act of translating the shaft assembly relative to the base includes rotating a spool to pay in one of a proximal insertion cable or a distal insertion cable and to pay out the other of the proximal insertion cable or distal insertion cables, wherein the act of translating the shaft assembly relative to the base includes translating the ultrasonic blade relative to the base to an ultrasonic blade over-extended position; and (b) actuating the clamp arm relative to the ultrasonic blade, wherein the act of actuating the clamp arm relative to the ultrasonic blade includes manipulating at least one closure pulley to cause a change of length of a closure cable within the base to thereby translate the dynamic tube relative to the static tube.

15. The method of claim 14, further comprising translating the shaft assembly relative to the base, wherein the act of translating the shaft assembly relative to the base includes rotating the spool to pay out the proximal insertion cable or the distal insertion cable previously paid in and to pay in the other of the proximal insertion cable or distal insertion cable previously paid out, wherein the act of translating the shaft assembly relative to the base includes translating the ultrasonic blade relative to the base to an ultrasonic blade extended position, the ultrasonic blade over-extended position being different than the ultrasonic blade extended position.

16. The method of claim 14, wherein the ultrasonic blade over-extended position is distal relative to the ultrasonic blade extended position.

17. The method of claim 14, wherein the ultrasonic surgical instrument further includes a proximal housing located proximally relative to the base.

18. The method of claim 17, wherein the act of actuating the clamp arm relative to the ultrasonic blade further includes translating the proximal housing distally relative to the base to a proximal housing over-extended position.

19. The method of claim 14, wherein the act of translating the shaft assembly relative to the base includes maintaining a constant length of the closure cable within the base.

* * * * *